US010865222B2

(12) United States Patent
Schoenhofen et al.

(10) Patent No.: US 10,865,222 B2
(45) Date of Patent: Dec. 15, 2020

(54) ***NEISSERIA GONORRHOEAE* THERAPEUTIC BASED ON CMP-NONULOSONATE SUGARS**

(71) Applicants: National Research Council of Canada, Ottawa (CA); University of Massachusetts Medical School, Boston, MA (US)

(72) Inventors: Ian Schoenhofen, Stittsville (CA); Dennis M. Whitfield, Ottawa (CA); Sanjay Ram, Worchester, MA (US)

(73) Assignees: National Research Council of Canada, Ottawa (CA); University of Massachusetts Medical School, Boston, MA (US)

( * ) Notice: Subject to any disclaimer, the term of this patent is extended or adjusted under 35 U.S.C. 154(b) by 0 days.

(21) Appl. No.: 15/693,852

(22) Filed: Sep. 1, 2017

(65) Prior Publication Data

US 2017/0362269 A1 Dec. 21, 2017

Related U.S. Application Data

(62) Division of application No. 14/627,396, filed on Feb. 20, 2015, now Pat. No. 9,765,106.

(60) Provisional application No. 61/942,389, filed on Feb. 20, 2014.

(51) Int. Cl.

| | |
|---|---|
| ***C07H 19/10*** | (2006.01) |
| ***A61K 31/7068*** | (2006.01) |
| ***C12Q 1/18*** | (2006.01) |

(52) U.S. Cl.

CPC ......... *C07H 19/10* (2013.01); *A61K 31/7068* (2013.01); *C12Q 1/18* (2013.01)

(58) Field of Classification Search

None

See application file for complete search history.

(56) References Cited

PUBLICATIONS

Fox et al. FEMS Microbiol.Lett. (1990) 66: 75-80 (Year: 1990).*

2015 Sexully Transmitted Disease Guidelines Gnoncoccal Inventions downloaded from the CDC from https://www.cdc.gov/std/tg2015/gonorrhea.htm on Dec. 26, 2019 (Year: 2015).*

Lewis et al. Infection and Immunity (2013) 81(1): 33-42 (Year: 2013).*

Mccutchan et al. J. Immunology (1978) 121(5): 1884-1888 (Year: 1978).*

Naim et al. J. Gen. Microbiol. (1988) 134: 3295-3306 (Year: 1988).*

McGee et al, Expression of Sialyltransferase Is Not Required for Interaction of Neisseria gonorrhoeae with Human Epithelial Cells and Human Neutrophils, Infection and Immunity, 1996, 64(10): 4129-4136.

Parsons et al, Resistance to Human Serum of Gonococci in Urethral Exudates is Reduced by Neuraminidase, Proceedings of the Royal Society of London B, 1990, 241(1300): 3-5.

* cited by examiner

*Primary Examiner* — Susan M Hanley

(74) *Attorney, Agent, or Firm* — Cermak Nakajima & McGowan LLP; Malcolm K. McGowan

(57) ABSTRACT

*N. gonorrhoeae* has become resistant to almost every conventional antibiotic. Described herein is the use of CMP-nonulosonate analogues to counter gonococcal complement evasion. The nonulosonate sugar is incorporated into the lipooligosaccharide of the *N. gonorrhoeae* which in turn reduces the serum resistance of the bacteria. This provides a novel therapeutic strategy against the global threat of multi-drug resistant gonorrhea.

18 Claims, 13 Drawing Sheets

*NEISSERIA GONORRHOEAE* THERAPEUTIC BASED ON CMP-NONULOSONATE SUGARS

The instant application is a divisional application of U.S. patent application Ser. No. 14/627,396, filed on Feb. 20, 2015, now U.S. Pat. No. 9,765,106, and claims the benefit of U.S. Provisional Patent Application Ser. No. 61/942,389, filed Feb. 20, 2014, the entire contents of which are hereby incorporated by reference.

GOVERNMENT LICENSE RIGHTS

This invention was made with government support under grant no. A1119327 awarded by the National Institutes of Health. The government has certain rights in the invention.

BACKGROUND OF THE INVENTION

Sialic acids are a family of 9 carbon sugars (belonging to a larger family of nonoses, or nonulosonates) expressed in the tissues of every vertebrate and several "higher-order" invertebrates (1). Sialic acids serve a wide variety of biological roles, including modulating several aspects of immune function (2). For example, cell surface-associated sialic acid inhibits complement activation. As an example of immune regulation, sheep erythrocytes are resistant to lysis by the alternative pathway because surface sialic acids increase the affinity of factor H (fH; inhibitor of the alternative pathway) (3). Neuraminidase treatment of sheep erythrocytes then reduces the affinity of fH, which permits complement activation and promotes hemolysis. Recent work showed that fH C-terminal domains 19 and 20 bound simultaneously to C3b (complement factor that binds microbial cell surfaces) and glycosaminoglycans (including sialic acids), respectively, on host cells, which served to inhibit the alternative pathway (4). Loss of sialic acids decreased fH binding and enhanced activation of the alternative pathway. Typically, fH binds vertebrate cell surfaces via sialic acids to allow preferential protection of host cells (i.e. reduce complement-mediated damage).

Many microbes express sialic acids, as well as other unique microbial nonulosonates (i.e. legionaminic (Leg) and pseudaminic (Pse) acid), on their surfaces that contribute to pathogenesis in several ways including subversion of complement activation, promoting biofilm formation and facilitating colonization (5). Some pathogens such as *Neisseria gonorrhoeae, Haemophilus influenzae, Histophilus somni* (*Haemophilus somnus*) and group A *N. meningitidis* lack the ability to synthesize sialic or nonulosonic acids, but scavenge these molecules (such as Neu5Ac or Neu5Gc, or the CMP-activated form CMP-Neu5Ac) from the host. Other pathogens, for example, *Escherichia coli* K1, *Streptococcus agalactiae*, groups B, C, W, and Y *N. meningitidis, Campylobacter jejuni* and certain Leptospira, can synthesize nonulosonic acids such as Neu5Ac, Leg5Ac7Ac or Pse5Ac7Ac de novo. Sialylation of gonococcal lacto-N-neotetraose (LNT) lipooligosaccharide (LOS) enhances resistance of *N. gonorrhoeae* to complement-dependent killing by decreasing binding of IgG against select bacterial targets such as the porin B (PorB) protein (6), which attenuates the classical pathway. LNT LOS sialylation also enhances fH binding, which results in inhibition of the alternative pathway (7).

U.S. Pat. Nos. 6,096,529 and 6,210,933 disclose that LacNAc may be modified with a sialic acid analogue using a recombinant sialyltransferase derived from *N. gonorrhoeae* or *N. meningitidis*. These patents do not specifically mention that the sialic acid analogue could be Leg5Ac7Ac.

U.S. Pat. No. 6,168,934 discloses the proposition that it is possible to sialylate LacNAc with a sialic acid analogue using an appropriate sialyltransferase (see col. 24, lines 7-66). The patent does not specifically disclose the use of a sialyltransferase from *Neisseria* spp. The patent also does not specifically mention that the sialic acid analogue could be Leg5Ac7Ac.

*N. gonorrhoeae* has become resistant to almost every conventional antibiotic. Over the past 3 years, resistance to ceftriaxone has ushered in an era of potentially untreatable gonorrhea. There is an urgent need for novel therapeutics and vaccines against this disease. LOS sialylation is an important aspect of gonococcal pathogenesis and isogenic mutants that lack the ability to sialylate their LOS are at a disadvantage in vivo compared to their wild-type counterparts (31). Disabling the ability of gonococci to siaylate their LOS represents a novel prophylactic or treatment strategy.

SUMMARY OF THE INVENTION

According to a first aspect of the invention, there is provided a method for treating or preventing a *N. gonorrhoeae* infection in an individual in need of such treatment comprising administering to said individual an effective amount of a cytidine 5'-monophospho-nonulosonate sugar of Formula (I):

(I)

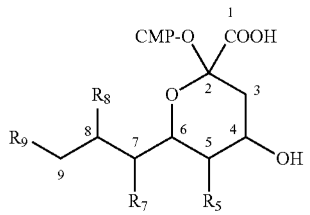

wherein:

$R_5$ is: OH, O-Acetyl, O-Methyl, $NH_2$, NH-Acetyl, NH-Glycolyl, NH-Prop, NH-But, NH-Pent, NH-Hex, NH-Hept, NH-Lev, NH—(O-Acetyl)glycolyl, NH—(O-Methyl)glycolyl, NH—(O-α2Neu5Gc)glycolyl, NH—(N-Methyl)acetimidoyl, NH-(di-N-Methyl)acetimidoyl, NH-(Glutam-4-yl)amino, NH—(N-Methyl-glutam-4-yl)amino, or NH-Azido-acetyl;

$R_7$ is: OH, $NH_2$, O-Acetyl, O-Methyl, O-Lactyl, NH-Acetyl, NH-Azido-acetyl, NH-(D-Alanyl), or NH—(N-Acetyl-D-alanyl);

$R_8$ is: OH, $NH_2$, $N_3$, O-Acetyl, O-Methyl, O-Lactyl, O-Sulfate, O-Sia, or O-Glc; and $R_9$ is: OH, O-Acetyl, $N_3$, $NH_2$, NH-Acetyl, NH-Thioacetyl, Benzamido [NHCOPh], NH-Gly, NH-Succ, $SCH_3$, $SO_2CH_3$, Hexanoylamido [$NHCO(CH_2)_4CH_3$], O-Methyl, O-Lactyl, O-Phosphate, O-Sulfate, O-Sia, or H.

In another aspect of the invention, there is provided a method for treating or preventing a *N. gonorrhoeae* infection in an individual in need of such treatment comprising administering to said individual an effective amount of a cytidine 5'-monophospho-nonulosonate sugar of Formula (I) wherein:

$R_5$ is: OH, NH-Acetyl, or NH-Glycolyl;

$R_7$ is: OH, O-Acetyl, O-Methyl, or NH-Acetyl;

$R_8$ is: OH, $NH_2$, $N_3$, O-Acetyl, O-Methyl, or O-Sulfate; and $R_9$ is: OH, O-Acetyl, $N_3$, $NH_2$, O-Methyl, O-Lactyl, O-Phosphate, O-Sulfate, or H.

In another aspect of the invention, there is provided a method for treating or preventing a *N. gonorrhoeae* infection in an individual in need of such treatment comprising administering to said individual an effective amount of a cytidine 5'-monophospho-nonulosonate sugar of Formula (I) wherein:

$R_5$ is: NH-Acetyl or NH-Glycolyl;

$R_7$ is: OH or NH-Acetyl;

$R_8$ is: OH or O-Methyl; and $R_9$ is: OH, O-Acetyl, $N_3$, or H.

In yet another aspect of the invention, there is provided a method for modifying a molecule with N,N'-diacetyllegionaminic acid (Leg5Ac7Ac) comprising: contacting an acceptor molecule bearing a terminal Galβ1,4GlcNAc residue with an activated sugar nucleotide of N,N'-diacetyllegionaminic acid (CMP-Leg5Ac7Ac) in the presence of a sialyltransferase derived from a *Neisseria* spp.

In another aspect of the invention, there is provided a method for identifying a cytidine 5'-monophospho-nonulosonate sugar capable of reducing virulence of *N. gonorrhoeae* comprising:

incubating *N. gonorrhoeae* with the cytidine 5'-monophospho-nonulosonate sugar of interest under conditions suitable for incorporation of nonulosonate sugar into lipooligosaccharide of the *N. gonorrhoeae*; and determining if serum resistance of the *N. gonorrhoeae* is reduced compared to an untreated control culture of *N. gonorrhoeae*.

In a further aspect, there is provided a method for treating or preventing a *N. gonorrhoeae* infection in an individual in need of such treatment comprising administering to said individual an effective amount of a cytidine 5'-monophospho-nonulosonate sugar, wherein the cytidine 5'-monophospho-nonulosonate sugar is a suitable substrate for the *N. gonorrhoeae* sialyltransferase Lst, whereby the respective nonulosonate sugar is incorporated within the *N. gonorrhoeae* LOS, which then reduces the serum resistance of *N. gonorrhoeae*, even in the presence of cytidine 5'-monophospho-N-acetylneuraminic acid (CMP-Neu5Ac).

As will be appreciated by one of skill in the art, CMP-nonulosonate is not incorporated into LOS, only the nonulosonate moiety of the CMP-nonulosonate is incorporated into the LOS.

As used herein, a "suitable substrate" for Lst refers to a CMP-nonulosonate sugar that the Lst enzyme can use as a donor to add the respective nonulosonate to the LOS acceptor.

The cytidine 5'-monophospho-nonulosonate sugar may be a cytidine 5'-monophospho-nonulosonate sugar, or pharmaceutically acceptable salt or derivative thereof, of Formula (I):

(I)

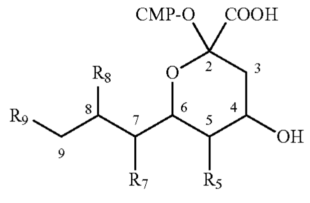

wherein:

$R_5$ is: OH, O-Acetyl, O-Methyl, $NH_2$, NH-Acetyl, NH-Glycolyl, NH-Prop, NH-But, NH-Pent, NH-Hex, NH-Hept, NH-Lev, NH—(O-Acetyl)glycolyl, NH—(O-Methyl)glycolyl, NH—(O-α2Neu5Gc)glycolyl, NH—(N-Methyl)acetimidoyl, NH-(di-N-Methyl)acetimidoyl, NH-(Glutam-4-yl) amino, NH—(N-Methyl-glutam-4-yl)amino, or NH-Azido-acetyl;

$R_7$ is: OH, $NH_2$, O-Acetyl, O-Methyl, O-Lactyl, NH-Acetyl, NH-Azido-acetyl, NH-(D-Alanyl), or NH—(N-Acetyl-D-alanyl);

$R_8$ is: OH, $NH_2$, $N_3$, O-Acetyl, O-Methyl, O-Lactyl, O-Sulfate, O-Sia, or O-Glc; and $R_9$ is: OH, O-Acetyl, $N_3$, $NH_2$, NH-Acetyl, NH-Thioacetyl, Benzamido [NHCOPh], NH-Gly, NH-Succ, $SCH_3$, $SO_2CH_3$, Hexanoylamido [$NHCO(CH_2)_4CH_3$], O-Methyl, O-Lactyl, O-Phosphate, O-Sulfate, O-Sia, or H.

In other embodiments, $R_5$ is: OH, NH-Acetyl, or NH-Glycolyl; $R_7$ is: OH, O-Acetyl, O-Methyl, or NH-Acetyl; $R_8$ is: OH, $NH_2$, $N_3$, O-Acetyl, O-Methyl, or O-Sulfate; and $R_9$ is: OH, O-Acetyl, $N_3$, $NH_2$, O-Methyl, O-Lactyl, O-Phosphate, 0-Sulfate, or H.

In yet other embodiments, $R_5$ is: NH-Acetyl or NH-Glycolyl; $R_7$ is: OH or NH-Acetyl; $R_8$ is: OH or O-Methyl; and $R_9$ is: OH, O-Acetyl, $N_3$, or H.

According to a further aspect of the invention, there is provided an effective amount of one or more of the cytidine 5'-monophospho-nonulosonate sugars defined above formulated for administration to an individual who has or is suspected of having or is at risk of an *N. gonorrhoeae* infection. The cytidine 5'-monophospho-nonulosonate sugar(s) may be formulated for oral, topical or intravenous administration.

In some embodiments, the cytidine 5'-monophospho-nonulosonate sugar is formulated for sustained release.

According to a yet further aspect of the invention, there is provided use of a cytidine 5'-monophospho-nonulosonate sugar to treat or prevent a *N. gonorrhoeae* infection in a subject individual in need of such treatment, wherein the cytidine 5'-monophospho-nonulosonate sugar is a compound of Formula (I):

(I)

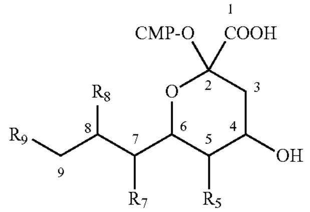

wherein:

$R_5$ is: OH, O-Acetyl, O-Methyl, $NH_2$, NH-Acetyl, NH-Glycolyl, NH-Prop, NH-But, NH-Pent, NH-Hex, NH-Hept, NH-Lev, NH—(O-Acetyl)glycolyl, NH—(O-Methyl)glycolyl, NH—(O-α2Neu5Gc)glycolyl, NH—(N-Methyl)acetimidoyl, NH-(di-N-Methyl)acetimidoyl, NH-(Glutam-4-yl) amino, NH—(N-Methyl-glutam-4-yl)amino, or NH-Azido-acetyl;

$R_7$ is: OH, $NH_2$, O-Acetyl, O-Methyl, O-Lactyl, NH-Acetyl, NH-Azido-acetyl, NH-(D-Alanyl), or NH—(N-Acetyl-D-alanyl);

$R_8$ is: OH, $NH_2$, $N_3$, O-Acetyl, O-Methyl, O-Lactyl, O-Sulfate, O-Sia, or O-Glc; and $R_9$ is: OH, O-Acetyl, $N_3$, $NH_2$, NH-Acetyl, NH-Thioacetyl, Benzamido [NHCOPh], NH-Gly, NH-Succ, $SCH_3$, $SO_2CH_3$, Hexanoylamido [$NHCO(CH_2)_4CH_3$], O-Methyl, O-Lactyl, O-Phosphate, O-Sulfate, O-Sia, or H.

In another aspect of the invention, there is provided use of a cytidine 5'-monophospho-nonulosonate sugar to treat or prevent a *N. gonorrhoeae* infection in an individual in need of such treatment, wherein the cytidine 5'-monophospho-nonulosonate sugar is a compound of Formula (I) wherein:

$R_5$ is: OH, NH-Acetyl, or NH-Glycolyl;

$R_7$ is: OH, O-Acetyl, O-Methyl, or NH-Acetyl;

$R_8$ is: OH, $NH_2$, $N_3$, O-Acetyl, O-Methyl, or O-Sulfate; and $R_9$ is: OH, O-Acetyl, $N_3$, $NH_2$, O-Methyl, O-Lactyl, O-Phosphate, O-Sulfate, or H.

In another aspect of the invention, there is provided use of a cytidine 5'-monophospho-nonulosonate sugar to treat or present a *N. gonorrhoeae* infection in an individual in need of such treatment, wherein the cytidine 5'-monophospho-nonulosonate sugar is a compound of Formula (I) wherein:

$R_5$ is: NH-Acetyl or NH-Glycolyl;

$R_7$ is: OH or NH-Acetyl;

$R_8$ is: OH or O-Methyl; and $R_9$ is: OH, O-Acetyl, $N_3$, or H.

F62 ΔlgtD grown in media containing CMP-nonulosonate analogues (2 μg/ml (~3 μM)). C. A comparison of fH binding to *N. gonorrhoeae* F62 ΔlgtD grown in CMP-Neu5Ac and CMP-Neu5Gc concentrations ranging from 0.5 μg/ml to 4 μg/ml. Bacteria were incubated with fH (1 μg/ml) and bound fH was detected by FACS using mAb 90×. Y-axis, median fluorescence. The mean (SD) of 2 independent experiments is shown.

Figure 10:
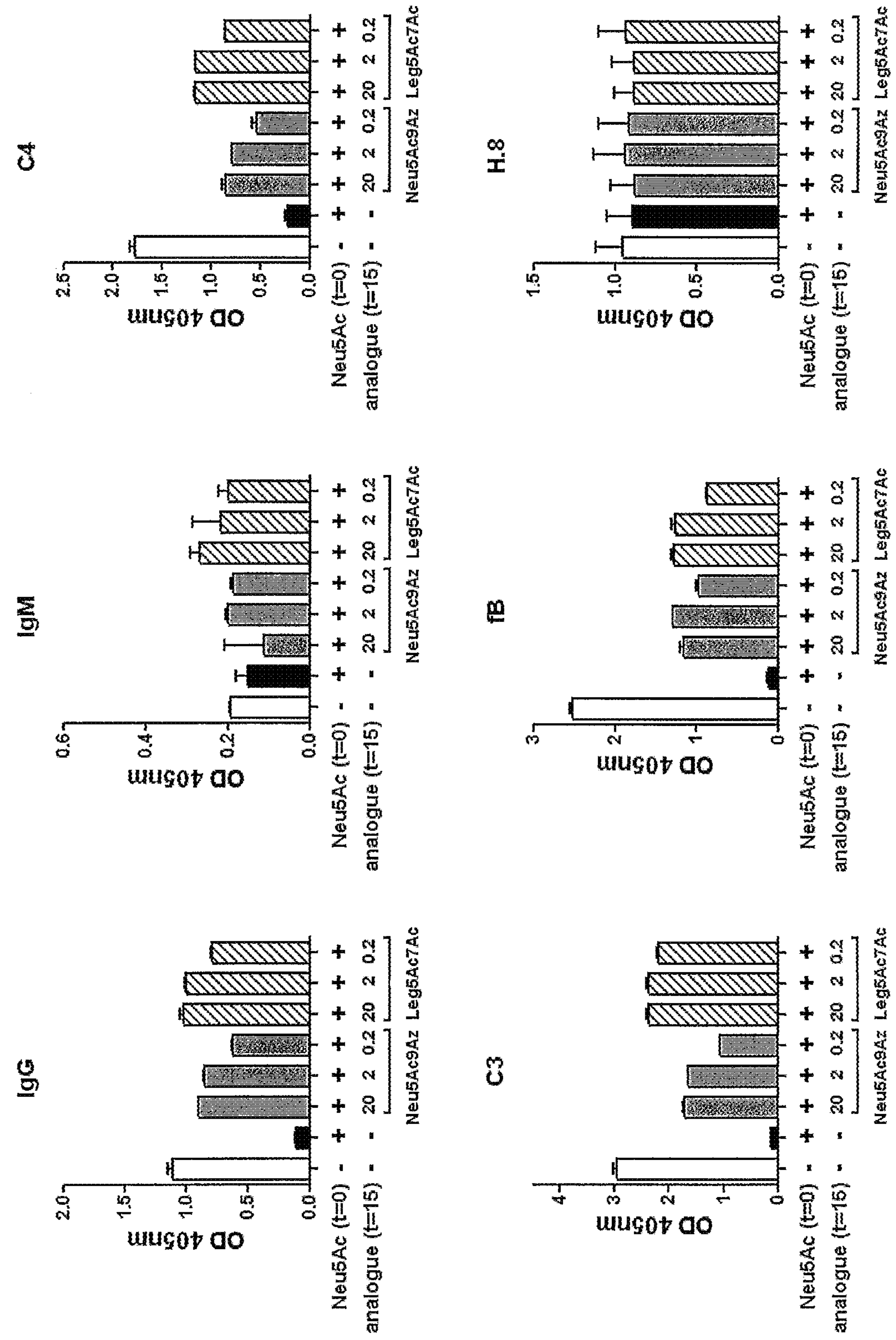

FIG. 10. CMP-Neu5Ac9Az and CMP-Leg5Ac7Ac interfere with inhibition of the classical and alternative pathways of complement mediated by CMP-Neu5Ac. *N. gonorrhoeae* F62 ΔlgtD was incubated with 20 μg/ml (~30 μM) CMP-Neu5Ac, followed in 15 min by the addition of CMP-Neu5Ac9Az or CMP-Leg5Ac7Ac (at concentrations of 20, 2 or 0.2 μg/ml final) for 2 h as described in FIG. 5. Bacteria were incubated in 3.3% NHS and Ab binding and complement deposition studies were carried out by ELISA. The mean (SD) of two independent experiments is shown.

Figure 11:
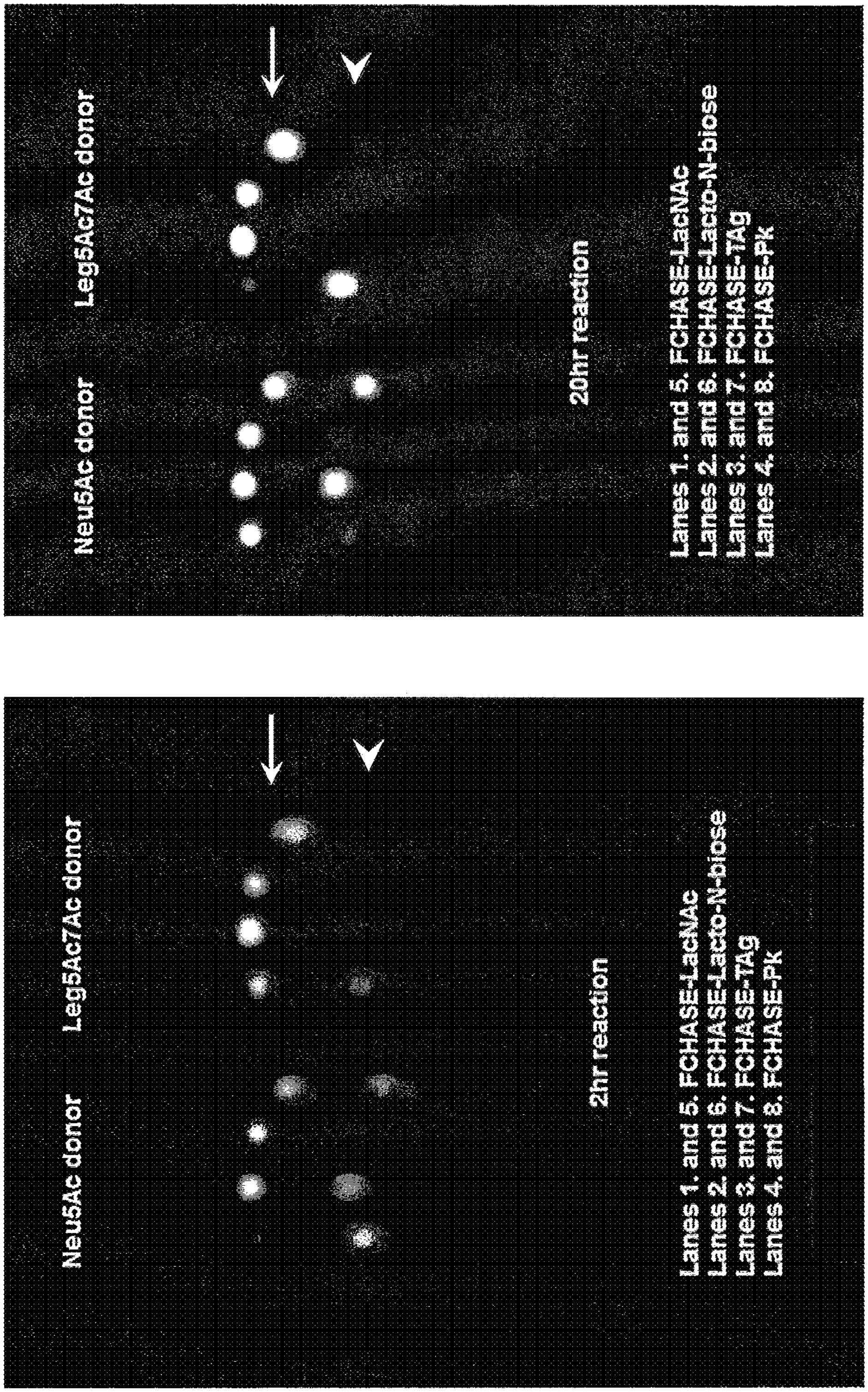

FIG. 11. *N. gonorrhoeae* Lst sialyltransferase efficiently legylates a LacNAc acceptor. The acceptor specificity of *N. gonorrhoeae* Lst sialyltransferase was assessed using CMP-Neu5Ac and CMP-Leg5Ac7Ac donors. The various acceptors tested were LacNAc or Galβ-1,4-GlcNAc-β-FCHASE, Lacto-N-biose or Galβ-1,3-GlcNAc-β-FCHASE, TAg or Galβ-1,3-GalNAc-α-FCHASE, and Pk or Galα-1,4-Galβ-1,4-Glc-β-FCHASE. Lst enzyme preparations (2.5 μg per assay) were incubated with 2.5 pmoles of each acceptor with either 3 mM CMP-Neu5Ac or 3 mM CMP-Leg5Ac7Ac for either 2 or 20 h as indicated. Reactions were then examined by TLC. Arrows indicate the general vicinity of FCHASE acceptors (top spots), whereas arrowheads indicate the general vicinity of modified FCHASE acceptors (bottom spots—enzyme product).

Figure 12:
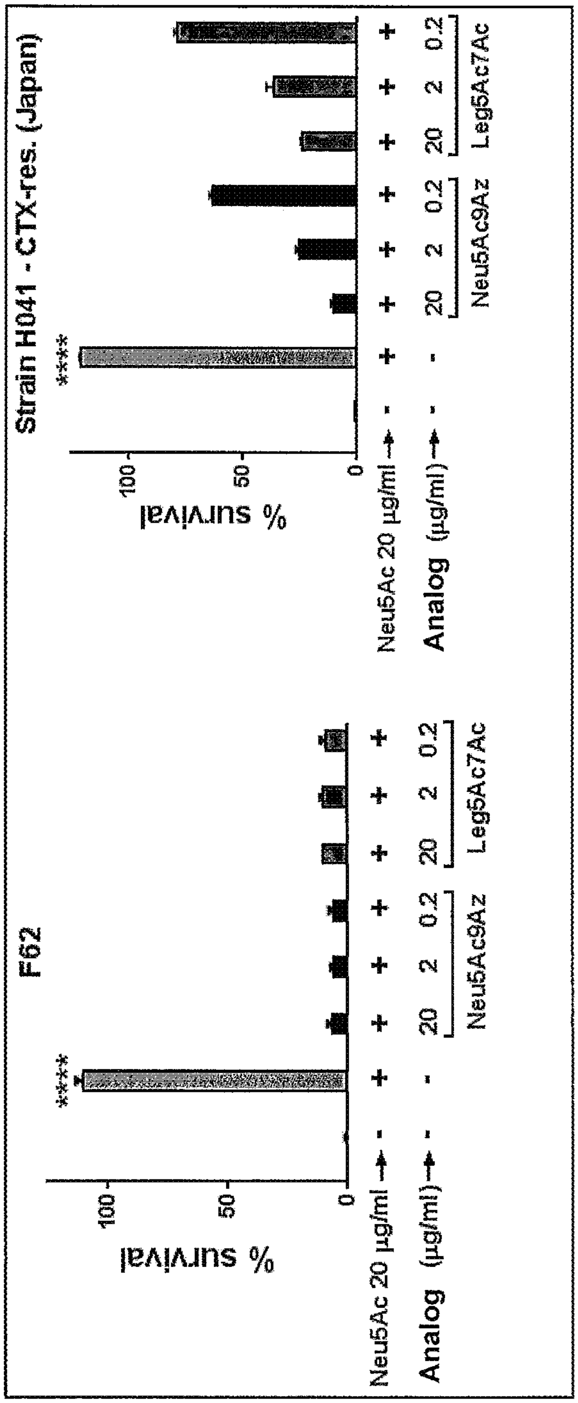

FIG. 12. CMP-Leg5Ac7Ac and CMP-Neu5Ac9Az counter serum resistance mediated by CMP-Neu5Ac. *N. gonorrhoeae* F62 ΔlgtD (left graph) and the *N. gonorrhoeae* antibiotic resistant 'superbug' H041 (right graph) were incubated in media containing CMP-Neu5Ac (20 μg/ml) followed in 15 min by the addition of either CMP-Neu5Ac9Az or CMP-Leg5Ac7Ac at concentrations of 0.2, 2 or 20 μg/ml. Bacteria were then grown for 2 h, and a serum bactericidal assay was performed (10% normal human serum). Y-axis, % survival at 30 min. The mean (SD) of 2 experiments is shown. ****, $P<0.0001$ compared to all other bars (1-way ANOVA, Dunnett's multiple comparisons.)

Figure 13:
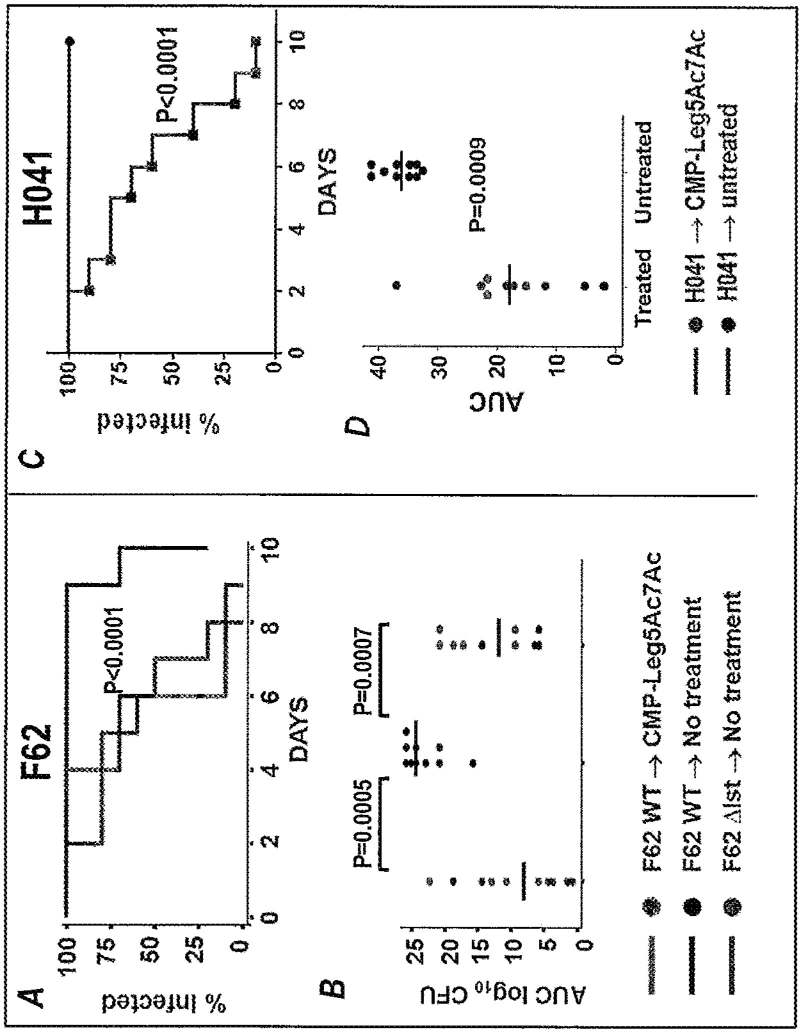

FIG. 13. Intravaginal CMP-Leg5Ac7Ac attenuates *N. gonorrhoeae* (Ng) infection in mice. A and B. Efficacy of CMP-Leg5Ac7Ac against Ng F62. 17β-estradiol treated BALB/c mice were infected with i) Ng F62 (wildtype [WT]) and treated (CMP-Leg5Ac7Ac, 10 μg intravaginally, daily), ii) Ng F62 WT→saline (No treatment) or iii) Ng F62 Δlst (cannot sialylate LOS), untreated. Ng load in the vagina was enumerated daily. A. Time to clearance. B. Area under the curve (AUC; each point represents the AUC of CFU vs. time for each mouse). Horizontal bar, geometric mean. C and D. Efficacy of CMP-Leg5Ac7Ac vs ceftriaxone-resistant isolate H041. Time to clearance (C) and AUC analysis (D) are described above.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Substitution of *N. gonorrhoeae* lacto-N-neotetraose (LNT) lipooligosaccharide (LOS) with Neu5Ac results in the ability of the bacterium to evade complement-mediated killing. Previous studies have shown that the addition of Neu5Ac to LNT LOS decreases binding of specific IgG and enhances binding of factor H (fH), an inhibitor of the alternative pathway of complement. As discussed below, using CMP salts of 6 nonulosonate analogues (Neu5Gc, Neu5Ac9Ac, Neu5Ac9Az, Neu5Gc8Me, Leg5Ac7Ac and Pse5Ac7Ac), it is shown that with the exception of CMP-Pse5Ac7Ac, all analogues served as substrates for gonococcal LOS sialyltransferase (Lst). Only CMP-Neu5Gc simulated the high-level serum resistance previously reported with CMP-Neu5Ac. CMP-Neu5Ac9Ac and CMP-Neu5Gc8Me permitted resistance to only 3.3%, but not 6.7% serum. Incorporation of Neu5Ac and Neu5Gc resulted in high level fH binding to bacteria, Neu5Ac9Ac addition resulted in low levels of fH binding, but none of the other analogues enhanced fH binding. Analysis of Ab to and complement component deposition on bacteria revealed inhibition of the classical pathway (measured by IgG binding and C4 deposition) that were proportional to serum resistance. Neu5Ac9Az and Leg5Ac7Ac did not block fH binding facilitated by Neu5Ac, but could block classical pathway suppression and serum resistance mediated by Neu5Ac even when CMP-Neu5Ac was present at a 100-fold molar excess.

Importantly, Neu5Ac9Az/Neu5Ac9Ac and Leg5Ac7Ac differ from Neu5Ac at carbon 9 and carbons 7 and 9, respectively. As well, Neu5Gc8Me differs from Neu5Gc at carbon 8. As such, carbons 7, 8 and 9 within the exocyclic moiety of nonulosonate sugars appear to play a critical role in the avoidance of serum mediated killing by *N. gonorrhoeae*, as evidenced by the enhanced serum-mediated killing with CMP-Neu5Ac9Az, CMP-Neu5Ac9Ac, CMP-Leg5Ac7Ac and CMP-Neu5Gc8Me, that was not observed with either CMP-Neu5Ac or CMP-Neu5Gc only feeding controls. In addition, the somewhat higher level of serum resistance observed with the analogue CMP-Neu5Ac9Ac in comparison to CMP-Neu5Ac9Az and CMP-Leg5Ac7Ac is likely a result of spontaneous breakdown of the 9OAc group (resulting in Neu5Ac), as this breakdown was observed in handling the CMP-Neu5Ac9Ac preparations. Since the Pse5Ac7Ac nonulosonate is stereochemically different from sialic acid and legionaminic acid at carbons 5, 7 and 8, then it is not surprising that the *N. gonorrhoeae* Lst sialyltransferase was unable to properly utilize this CMP-sugar for LOS modification, and hence served as an excellent negative control (similar to no CMP-nonulosonate feeding control).

Collectively, these data shed light on substrate specificity of gonococcal Lst sialyltransferase and reveal critical roles for carbon 7, 8 and 9 substitutions for sialic acid-mediated gonococcal serum resistance. The use of CMP-nonulosonate analogues to counter gonococcal complement evasion provides a novel therapeutic strategy against the global threat of multi-drug resistant gonorrhea.

Figure 1:
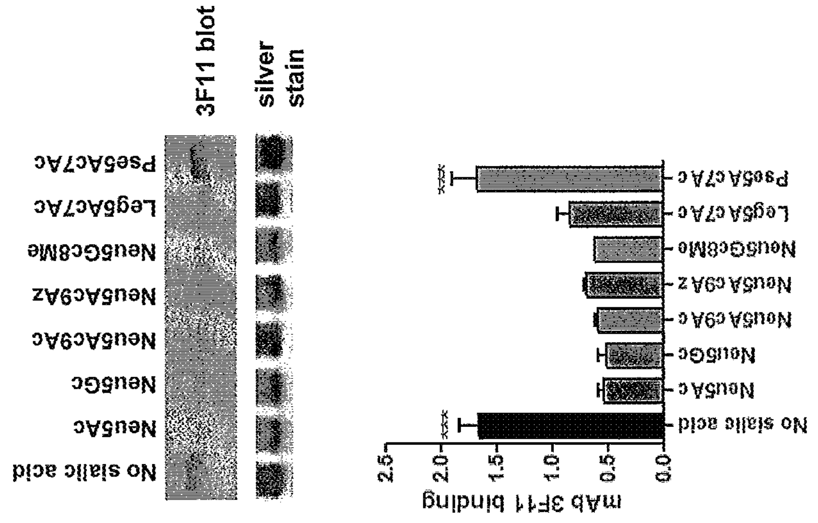
FIG. 1. Substrate specificity of gonococcal LOS sialyltransferase (Lst) *N. gonorrhoeae* strain F62 ΔlgtD was grown in standard gonococcal liquid media alone ('No sialic acid') or in media supplemented with CMP salts of the indicated sialic acid or nonulosonic acid, each at a concentration of 20 μg/ml (~30 μM), for 2 h at 37° C. Bacteria were washed, pellets treated with protease K, lysed in 4×LDS buffer and lysates were separated on 12% Bis-Tris gels using MES running buffer. LOS was transferred to a PVDF membrane and probed with mAb 3F11 that recognizes the lacto-N-neotetraose only in the non-sialylated state; the addition of a sialic acid or nonulosonate residue abrogates mAb 3F11 binding (upper panel). LOS was also visualized by silver staining (middle panel). Sialylation or nonulosonate (NulO) modification was also quantified using whole cell ELISA with mAb 3F11 (lower graph).
Figure 2:
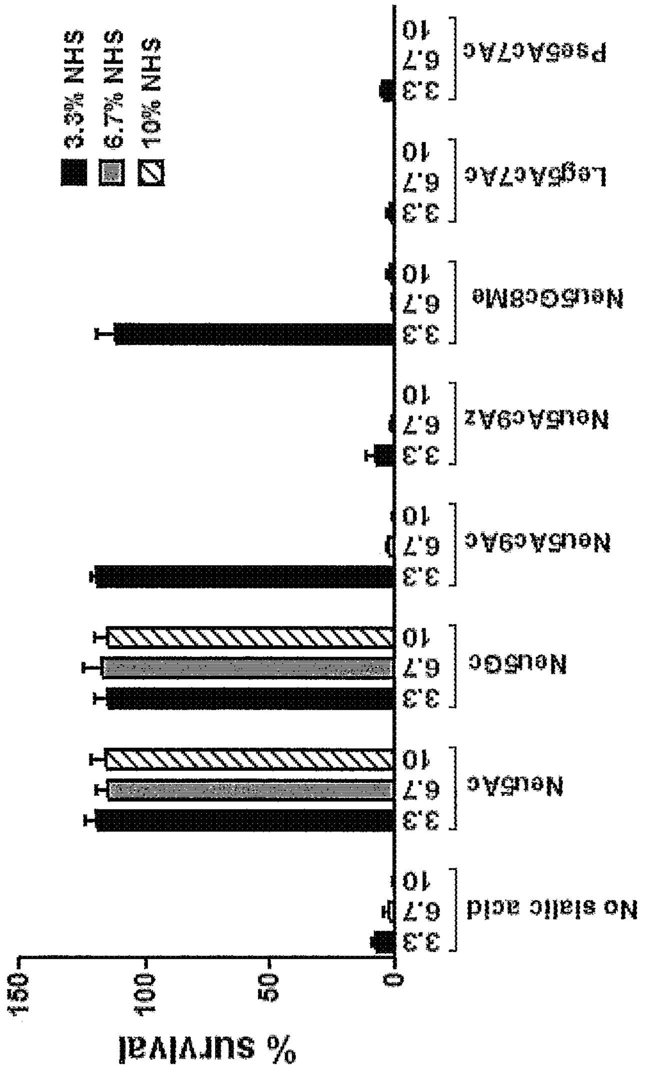
FIG. 2. Select nonulosonate analogues enhance gonococcal serum resistance. *N. gonorrhoeae* F62 ΔlgtD was grown in media alone (no CMP-sialic acid added), or media that contained 20 μg/ml (~30 μM) of each of the indicated CMP-nonulosonates. Resistance of bacteria to complement-dependent killing in the presence of 3.3%, 6.7% or 10% normal human serum (NHS) was measured in serum bactericidal assays. The mean (SD) of two independent experiments is shown.
Figure 6:
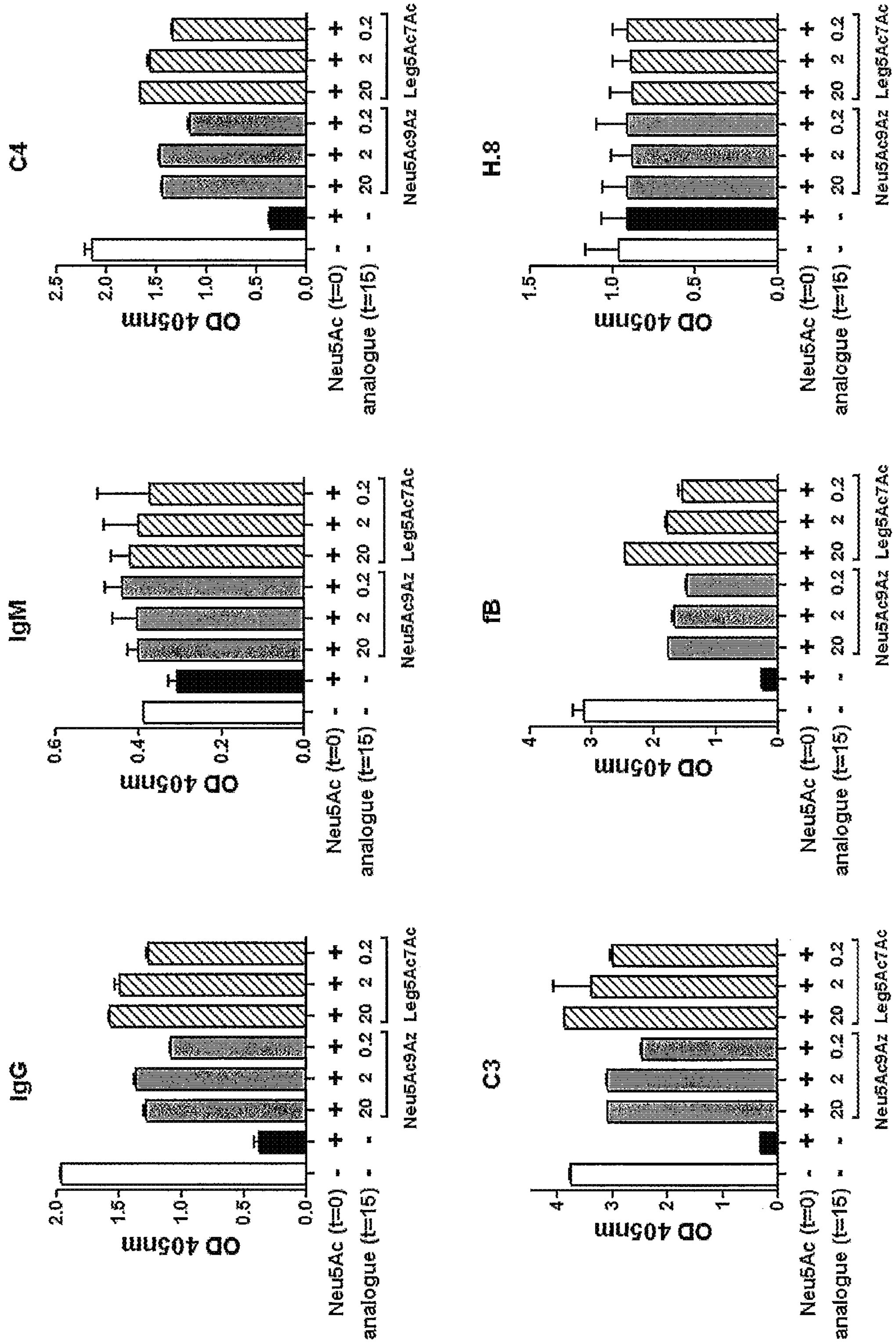
FIG. 6. CMP-Neu5Ac9Az and CMP-Leg5Ac7Ac interfere with inhibition of the classical and alternative pathways of complement mediated by CMP-Neu5Ac. *N. gonorrhoeae* F62 ΔlgtD was incubated with 20 μg/ml (~30 μM) CMP-Neu5Ac, followed in 15 min by the addition of CMP-Neu5Ac9Az or CMP-Leg5Ac7Ac (at concentrations of 20, 2 or 0.2 μg/ml final) and bacteria were incubated for 2 h as described in FIG. 5. Bacteria were incubated in 10% NHS and Ab binding and complement deposition studies were carried out by ELISA as described in FIG. 4. The mean (SD) of two independent experiments is shown.

As discussed herein, CMP-Neu5Ac9Az and CMP-Leg5Ac7Ac result in serum mediated killing even in the presence of low quantities of normal human sera (i.e. killing at 3.3% NHS as well as 6.7% and 10% NHS). Of the analogues that got incorporated within *N. gonorrhoeae* LOS, Leg5Ac7Ac seemed to be the least incorporated (FIG. 1), but provided just as good serum killing as Neu5Ac9Az modified LOS (FIG. 2). Neu5Ac9Az and Leg5Ac7Ac incorporation did not block factor H binding facilitated by Neu5Ac (FIG. 7A), but could block classical pathway suppression and serum resistance mediated by Neu5Ac (i.e. Neu5Ac treatment has less IgG binding and C4 deposition than treatment with the other analogues; FIGS. 6 and 10).

While not wishing to be bound to a particular theory or hypothesis, it is believed that the incorporated competing nonulosonates exert a 'dominant suppressive' effect over Neu5Ac. Here, the interplay between 7/8/9 modified nonulosonates and other Neu5Ac molecules present may negate their protective role. For example, only a few of these analogs are necessary to disrupt the ability of Neu5Ac to decrease IgG binding to bacterial surface targets. Reduced IgG binding could account, at least in part, for classical pathway regulation mediated by Neu5Ac. Two optimally spaced Fc domains of complement-fixing IgG subclasses can engage a C1 complex to initiate classical pathway activation. An arithmetic increase in the number of IgG molecules bound results in a geometric increase in the number of 'suitable pairs' of Fc domains to initiate the classical pathway. Thus, relatively small changes in IgG binding could lead to disproportionately greater differences in C4 fragment deposition and downstream complement activation.

Described herein is the use of certain CMP-nonulosonate sugars to treat *N. gonorrhoeae* infections.

For example, the CMP-nonulosonate sugar for treating or preventing a *N. gonorrhoeae* infection may be a cytidine 5'-monophospho-nonulosonate sugar of Formula (I) or a pharmaceutically acceptable salt or derivative thereof:

(I)

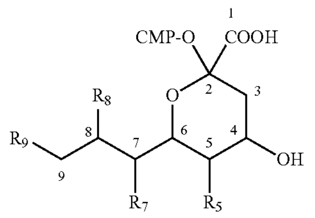

wherein:

$R_5$ is: OH, O-Acetyl, O-Methyl, $NH_2$, NH-Acetyl, NH-Glycolyl, NH-Prop, NH-But, NH-Pent, NH-Hex, NH-Hept, NH-Lev, NH—(O-Acetyl)glycolyl, NH—(O-Methyl)glycolyl, NH—(O-α2Neu5Gc)glycolyl, NH—(N-Methyl)acetimidoyl, NH-(di-N-Methyl)acetimidoyl, NH-(Glutam-4-yl)amino, NH—(N-Methyl-glutam-4-yl)amino, or NH-Azido-acetyl;

$R_7$ is: OH, $NH_2$, O-Acetyl, O-Methyl, O-Lactyl, NH-Acetyl, NH-Azido-acetyl, NH-(D-Alanyl), or NH—(N-Acetyl-D-alanyl);

$R_8$ is: OH, $NH_2$, $N_3$, O-Acetyl, O-Methyl, O-Lactyl, O-Sulfate, O-Sia, or O-Glc; and $R_9$ is: OH, O-Acetyl, $N_3$, $NH_2$, NH-Acetyl, NH-Thioacetyl, Benzamido [NHCOPh], NH-Gly, NH-Succ, $SCH_3$, $SO_2CH_3$, Hexanoylamido [$NHCO(CH_2)_4CH_3$], O-Methyl, O-Lactyl, O-Phosphate, O-Sulfate, O-Sia, or H.

In other embodiments:

$R_5$ is: OH, NH-Acetyl, or NH-Glycolyl;

$R_7$ is: OH, O-Acetyl, O-Methyl, or NH-Acetyl;

$R_8$ is: OH, $NH_2$, $N_3$, O-Acetyl, O-Methyl, or O-Sulfate; and $R_9$ is: OH, O-Acetyl, $N_3$, $NH_2$, O-Methyl, O-Lactyl, O-Phosphate, O-Sulfate, or H.

In yet other embodiments:

$R_5$ is: NH-Acetyl or NH-Glycolyl;

$R_7$ is: OH or NH-Acetyl;

$R_8$ is: OH or O-Methyl; and $R_9$ is: OH, O-Acetyl, $N_3$, or H.

In other embodiments, the compounds of the present invention may be, but are not necessarily limited to CMP-Nonulosonate (CMP-NulO) sugars, where the nonulosonates are selected from:

5,7-diacetamido-3,5,7,9-tetradeoxy-D-glycero-D-galacto-nonulosonic acid (Leg5Ac7Ac) ($R_5$=NH-Acetyl, $R_7$=NH-Acetyl, $R_8$=OH, $R_9$=H);

5,7-diacetamido-9-azido-3,5,7,9-tetradeoxy-D-glycero-D-galacto-nonulosonic acid (Leg5Ac7Ac9Az) ($R_5$=NH-Acetyl, $R_7$=NH-Acetyl, $R_8$=OH, $R_9$=$N_3$);

5,7-diacetamido-8-amino-3,5,7,8,9-pentadeoxy-D-glycero-D-galacto-nonulosonic acid (Leg5Ac7Ac8N) ($R_5$=NH-Acetyl, $R_7$=NH-Acetyl, $R_8$=$NH_2$, $R_9$=H);

5-acetamido-9-azido-3,5,9-trideoxy-D-glycero-D-galacto-nonulosonic acid (Neu5Ac9Az) ($R_5$=NH-Acetyl, $R_7$=OH, $R_8$=OH, $R_9$=$N_3$);

5-hydroxyacetamido-9-azido-3,5,9-trideoxy-D-glycero-D-galacto-nonulosonic acid (Neu5Gc9Az) ($R_5$=NH-Glycolyl, $R_7$=OH, $R_8$=OH, $R_9$=$N_3$);

5-acetamido-9-O-acetyl-3,5-dideoxy-D-glycero-D-galacto-nonulosonic acid (Neu5Ac9Ac) ($R_5$=NH-Acetyl, $R_7$=OH, $R_8$=OH, $R_9$=O-Acetyl);

5-hydroxyacetamido-9-O-acetyl-3,5-dideoxy-D-glycero-D-galacto-nonulosonic acid (Neu5Gc9Ac) ($R_5$=NH-Glycolyl, $R_7$=OH, $R_8$=OH, $R_9$=O-Acetyl);

2-keto-3-deoxy-9-O-acetyl-D-glycero-D-galacto-nonulosonic acid (Kdn9Ac) ($R_5$=OH, $R_7$=OH, $R_8$=OH, $R_9$=O-Acetyl);

5-acetamido-8-O-methyl-3,5-dideoxy-D-glycero-D-galacto-nonulosonic acid (Neu5Ac8Me) ($R_5$=NH-Acetyl, $R_7$=OH, $R_8$=O-Methyl, $R_9$=OH);

5-hydroxyacetamido-8-O-methyl-3,5-dideoxy-D-glycero-D-galacto-nonulosonic acid (Neu5Gc8Me) ($R_5$=NH-Glycolyl, $R_7$=OH, $R_8$=O-Methyl, $R_9$=OH);

5-acetamido-9-O-methyl-3,5-dideoxy-D-glycero-D-galacto-nonulosonic acid (Neu5Ac9Me) ($R_5$=NH-Acetyl, $R_7$=OH, $R_8$=OH, $R_9$=O-Methyl);

5-hydroxyacetamido-9-O-methyl-3,5-dideoxy-D-glycero-D-galacto-nonulosonic acid (Neu5Gc9Me) ($R_5$=NH-Glycolyl, $R_7$=OH, $R_8$=OH, $R_9$=O-Methyl);

2-keto-3-deoxy-9-O-methyl-D-glycero-D-galacto-nonulosonic acid (Kdn9Me) ($R_5$=OH, $R_7$=OH, $R_8$=OH, $R_9$=O-Methyl);

5-acetamido-9-O-lactyl-3,5-dideoxy-D-glycero-D-galacto-nonulosonic acid (Neu5Ac9Lt) ($R_5$=NH-Acetyl, $R_7$=OH, $R_8$=OH, $R_9$=O-Lactyl);

5-hydroxyacetamido-9-O-lactyl-3,5-dideoxy-D-glycero-D-galacto-nonulosonic acid (Neu5Gc9Lt) ($R_5$=NH-Glycolyl, $R_7$=OH, $R_8$=OH, $R_9$=O-Lactyl);

5-acetamido-9-O-phosphate-3,5-dideoxy-D-glycero-D-galacto-nonulosonic acid (Neu5Ac9$PO_4$) ($R_5$=NH-Acetyl, $R_7$=OH, $R_8$=OH, $R_9$=O-Phosphate);

5-hydroxyacetamido-9-O-phosphate-3,5-dideoxy-D-glycero-D-galacto-nonulosonic acid (Neu5Gc9$PO_4$) ($R_5$=NH-Glycolyl, $R_7$=OH, $R_8$=OH, $R_9$=O-Phosphate);

5-acetamido-9-O-sulfate-3,5-dideoxy-D-glycero-D-galacto-nonulosonic acid (Neu5Ac9$SO_4$) ($R_5$=NH-Acetyl, $R_7$=OH, $R_8$=OH, $R_9$=O-Sulfate);

5-hydroxyacetamido-9-O-sulfate-3,5-dideoxy-D-glycero-D-galacto-nonulosonic acid (Neu5Gc9$SO_4$) ($R_5$=NH-Glycolyl, $R_7$=OH, $R_8$=OH, $R_9$=O-Sulfate);

5-acetamido-8-O-sulfate-3,5-dideoxy-D-glycero-D-galacto-nonulosonic acid (Neu5Ac8$SO_4$) ($R_5$=NH-Acetyl, $R_7$=OH, $R_8$=O-Sulfate, $R_9$=OH);

5-hydroxyacetamido-8-O-sulfate-3,5-dideoxy-D-glycero-D-galacto-nonulosonic acid (Neu5Gc8$SO_4$) ($R_5$=NH-Glycolyl, $R_7$=OH, $R_8$=O-Sulfate, $R_9$=OH);

5-acetamido-8-O-acetyl-3,5-dideoxy-D-glycero-D-galacto-nonulosonic acid (Neu5Ac8Ac) ($R_5$=NH-Acetyl, $R_7$=OH, $R_8$=O-Acetyl, $R_9$=OH);

5-hydroxyacetamido-8-O-acetyl-3,5-dideoxy-D-glycero-D-galacto-nonulosonic acid (Neu5Gc8Ac) ($R_5$=NH-Glycolyl, $R_7$=OH, $R_8$=O-Acetyl, $R_9$=OH);

5-acetamido-9-amino-3,5,9-trideoxy-D-glycero-D-galacto-nonulosonic acid (Neu5Ac9N) or ($R_5$=NH-Acetyl, $R_7$=OH, $R_8$=OH, $R_9$=$NH_2$).

Alternatively, the compound may be a pharmaceutically acceptable salt or derivative of any one of the CMP-nonulosonate sugars listed above and elsewhere herein.

In other embodiments, the compounds of the present invention may be, but are not necessarily limited to CMP-nonulosonate (CMP-NulO) sugars, where the nonulosonates are selected from:

5,7-diacetamido-3,5,7,9-tetradeoxy-D-glycero-D-galacto-nonulosonic acid (Leg5Ac7Ac);

5-acetamido-9-azido-3,5,9-trideoxy-D-glycero-D-galacto-nonulosonic acid (Neu5Ac9Az);

5-acetamido-9-O-acetyl-3,5-dideoxy-D-glycero-D-galacto-nonulosonic acid (Neu5Ac9Ac);

5-hydroxyacetamido-8-O-methyl-3,5-dideoxy-D-glycero-D-galacto-nonulosonic acid (Neu5Gc8Me); or pharmaceutically acceptable salts or derivatives thereof.

Reference to several known CMP-sugars and methods of synthesis thereof can be found at least in references 40-50 and are incorporated herein by reference.

As will be appreciated by one of skill in the art, incorporation of these nonulosonate sugars by infective *N. gonorrhoeae* will result in the bacterium being unable to block the classical pathway, as discussed herein, resulting in reduced virulence of the bacterium. As discussed herein, these CMP-nonulosonate sugars can be incorporated into products for use by high-risk groups (for example, commercial sex workers) where it could decrease the transmission of disease. This could also have an indirect impact on HIV co-transmission, as will be known to those of skill in the art.

As will be appreciated by one of skill in the art, an "effective amount" is an amount of the CMP-nonulosonate sugar that is sufficient to treat a *N. gonorrhoeae* infection, that is, to accomplish at least one of the following: reduce virulence of *N. gonorrhoeae*, reduce the rate of transmission of *N. gonorrhoeae*, and reduce the severity of one or more symptoms associated with *N. gonorrhoeae* infection, for example, burning sensation during urination, painful or swollen testicles and increased vaginal discharge.

As will be appreciated by one of skill in the art, "sustained release" refers to the release of a drug or compound at a predetermined rate in order to maintain a specific concentration for a specific period of time. Sustained release formulations are well known in the art and may comprise for example a hydrogel, liposomes or a polymer.

In some embodiments, the formulation may include or may further comprise enzymatic inhibitors, pH modulating compounds, buffers, salt formation, solubilizers, excipients, emulsifiers, surfactants and/or antioxidants or the like. Such pharmaceutical compositions are also envisioned and are within the scope of the invention. For example, the formulation may include a sialyltransferase, for example, Lst or another suitable sialyltransferase in the formulation.

Suitable products will be readily apparent to one of skill in the art. For example, one or more of the CMP-nonulosonate sugars of the invention may be formulated for intravenous or topical administration, as discussed herein.

For oral administration, the CMP-nonulosonate sugar(s) may be formulated in a tablet, coated tablet, capsule or other similar form known in the art for oral administration of medicaments.

For topical administration, the CMP-nonulosonate sugar(s) may be formulated in a spray, cream, lotion, ointment or similar product. In other embodiments, the CMP-nonulosonate sugar(s) may be formulated for release from a prophylactic device. Examples of suitable prophylactic devices include but are by no means limited to condoms, cervical caps, contraceptive diaphragms and the like.

As will be appreciated by one of skill in the art, in some embodiments of the invention, the formulation comprises an effective amount of one or more of the cytidine 5'-monophospho-nonulosonate sugars and is used as a treatment for an individual who has or is suspected of having or is at risk of a *N. gonorrhoeae* infection. For example, the cytidine 5'-monophospho-nonulosonate sugars may be incorporated into a formulation as disclosed herein and formulated as a medicament for treatment of a *N. gonorrhoeae* infection. For example, the medicament comprising the cytidine 5'-monophospho-nonulosonate sugars may be formulated for oral, intravenous administration or for topical administration. As discussed herein, the medicament may also be formulated for sustained release.

In other embodiments of the invention, there is provided a prophylactic device coated or filled with an effective amount of one or more of the cytidine 5'-monophospho-nonulosonate sugars defined above for treating an individual who has or is suspected of having or is at risk of an *N. gonorrhoeae* infection. In some embodiments, the cytidine 5'-monophospho-nonulosonate sugar is formulated for sustained release, as discussed above.

According to an aspect of the invention, there is provided use of a cytidine 5'-monophospho-nonulosonate sugar for I.V./topically treating a *N. gonorrhoeae* infection in a human subject, wherein the cytidine 5'-monophospho-nonulosonate sugar is a suitable substrate for the *N. gonorrhoeae* sialyltransferase Lst, whereby the respective nonulosonate sugar is incorporated within the *N. gonorrhoeae* LOS, which then reduces the serum resistance of *N. gonorrhoeae*, even in the presence of cytidine 5'-monophospho-N-acetylneuraminic acid (CMP-Neu5Ac).

According to another aspect of the invention, there is provided a method for I.V./topically treating a *N. gonorrhoeae* infection in an individual in need of such treatment comprising administering to said individual an effective amount of a cytidine 5'-monophospho-nonulosonate sugar, wherein the cytidine 5'-monophospho-nonulosonate sugar is a suitable substrate for the *N. gonorrhoeae* sialyltransferase Lst, whereby the respective nonulosonate sugar is incorporated within the *N. gonorrhoeae* LOS, which then reduces the serum resistance of *N. gonorrhoeae*, even in the presence of cytidine 5'-monophospho-N-acetylneuraminic acid (CMP-Neu5Ac).

An "individual in need of such treatment" refers to an individual who has or is suspected of having or is at risk of an *N. gonorrhoeae* infection.

As will be appreciated by one of skill in the art, an individual who is "at risk" of a *N. gonorrhoeae* infection is an individual who may have sexual contact with a person who may be infected by *N. gonorrhoeae*.

According to a further aspect of the invention, there is provided use of a cytidine 5'-monophospho-nonulosonate sugar of Formula (I) or a pharmaceutically acceptable salt or derivative thereof to treat or prevent a *N. gonorrhoeae* infection in a human subject.

The cytidine 5'-monophospho-nonulosonate sugar may be a cytidine 5'-monophospho-nonulosonate sugar of Formula (I):

(I)

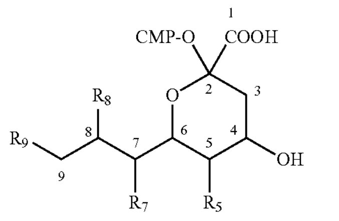

wherein:

$R_5$ is: OH, O-Acetyl, O-Methyl, $NH_2$, NH-Acetyl, NH-Glycolyl, NH-Prop, NH-But, NH-Pent, NH-Hex, NH-Hept, NH-Lev, NH—(O-Acetyl)glycolyl, NH—(O-Methyl)glycolyl, NH—(O-α2Neu5Gc)glycolyl, NH—(N-Methyl)acetimidoyl, NH-(di-N-Methyl)acetimidoyl, NH-(Glutam-4-yl) amino, NH—(N-Methyl-glutam-4-yl)amino, or NH-Azido-acetyl;

$R_7$ is: OH, $NH_2$, O-Acetyl, O-Methyl, O-Lactyl, NH-Acetyl, NH-Azido-acetyl, NH-(D-Alanyl), or NH—(N-Acetyl-D-alanyl);

$R_8$ is: OH, $NH_2$, $N_3$, O-Acetyl, O-Methyl, O-Lactyl, O-Sulfate, O-Sia, or O-Glc; and $R_9$ is: OH, O-Acetyl, $N_3$, $NH_2$, NH-Acetyl, NH-Thioacetyl, Benzamido [NHCOPh], NH-Gly, NH-Succ, $SCH_3$, $SO_2CH_3$, Hexanoylamido [$NHCO(CH_2)_4CH_3$], O-Methyl, O-Lactyl, O-Phosphate, O-Sulfate, O-Sia, or H.

In other embodiments:

$R_5$ is: OH, NH-Acetyl, or NH-Glycolyl;

$R_7$ is: OH, O-Acetyl, O-Methyl, or NH-Acetyl;

$R_8$ is: OH, $NH_2$, $N_3$, O-Acetyl, O-Methyl, or O-Sulfate; and $R_9$ is: OH, O-Acetyl, $N_3$, $NH_2$, O-Methyl, O-Lactyl, O-Phosphate, O-Sulfate, or H.

In yet other embodiments:

$R_5$ is: NH-Acetyl or NH-Glycolyl;

$R_7$ is: OH or NH-Acetyl;

$R_8$ is: OH or O-Methyl; and $R_9$ is: OH, O-Acetyl, $N_3$, or H.

In other embodiments, the compounds of the present invention may be, but are not necessarily limited to CMP-Nonulosonate (CMP-NulO) sugars, where the nonulosonates are selected from:

5,7-diacetamido-3,5,7,9-tetradeoxy-D-glycero-D-galacto-nonulosonic acid (Leg5Ac7Ac) ($R_5$=NH-Acetyl, $R_7$=NH-Acetyl, $R_8$=OH, $R_9$=H);

5,7-diacetamido-9-azido-3,5,7,9-tetradeoxy-D-glycero-D-galacto-nonulosonic acid (Leg5Ac7Ac9Az) ($R_5$=NH-Acetyl, $R_7$=NH-Acetyl, $R_8$=OH, $R_9$=$N_3$);

5,7-diacetamido-8-amino-3,5,7,8,9-pentadeoxy-D-glycero-D-galacto-nonulosonic acid (Leg5Ac7Ac8N) ($R_5$=NH-Acetyl, $R_7$=NH-Acetyl, $R_8$=$NH_2$, $R_9$=H);

5-acetamido-9-azido-3,5,9-trideoxy-D-glycero-D-galacto-nonulosonic acid (Neu5Ac9Az) ($R_5$=NH-Acetyl, $R_7$=OH, $R_8$=OH, $R_9$=$N_3$);

5-hydroxyacetamido-9-azido-3,5,9-trideoxy-D-glycero-D-galacto-nonulosonic acid (Neu5Gc9Az) ($R_5$=NH-Glycolyl, $R_7$=OH, $R_8$=OH, $R_9$=$N_3$);

5-acetamido-9-O-acetyl-3,5-dideoxy-D-glycero-D-galacto-nonulosonic acid (Neu5Ac9Ac) ($R_5$=NH-Acetyl, $R_7$=OH, $R_8$=OH, $R_9$=O-Acetyl);

5-hydroxyacetamido-9-O-acetyl-3,5-dideoxy-D-glycero-D-galacto-nonulosonic acid (Neu5Gc9Ac) ($R_5$=NH-Glycolyl, $R_7$=OH, $R_8$=OH, $R_9$=O-Acetyl);

2-keto-3-deoxy-9-O-acetyl-D-glycero-D-galacto-nonulosonic acid (Kdn9Ac) ($R_5$=OH, $R_7$=OH, $R_8$=OH, $R_9$=O-Acetyl);

5-acetamido-8-O-methyl-3,5-dideoxy-D-glycero-D-galacto-nonulosonic acid (Neu5Ac8Me) ($R_5$=NH-Acetyl, $R_7$=OH, $R_8$=O-Methyl, $R_9$=OH);

5-hydroxyacetamido-8-O-methyl-3,5-dideoxy-D-glycero-D-galacto-nonulosonic acid (Neu5Gc8Me) ($R_5$=NH-Glycolyl, $R_7$=OH, $R_8$=O-Methyl, $R_9$=OH);

5-acetamido-9-O-methyl-3,5-dideoxy-D-glycero-D-galacto-nonulosonic acid (Neu5Ac9Me) ($R_5$=NH-Acetyl, $R_7$=OH, $R_8$=OH, $R_9$=O-Methyl);

5-hydroxyacetamido-9-O-methyl-3,5-dideoxy-D-glycero-D-galacto-nonulosonic acid (Neu5Gc9Me) ($R_5$=NH-Glycolyl, $R_7$=OH, $R_8$=OH, $R_9$=O-Methyl);

2-keto-3-deoxy-9-O-methyl-D-glycero-D-galacto-nonulosonic acid (Kdn9Me) ($R_5$=OH, $R_7$=OH, $R_8$=OH, $R_9$=O-Methyl);

5-acetamido-9-O-lactyl-3,5-dideoxy-D-glycero-D-galacto-nonulosonic acid (Neu5Ac9Lt) ($R_5$=NH-Acetyl, $R_7$=OH, $R_8$=OH, $R_9$=O-Lactyl);

5-hydroxyacetamido-9-O-lactyl-3,5-dideoxy-D-glycero-D-galacto-nonulosonic acid (Neu5Gc9Lt) ($R_5$=NH-Glycolyl, $R_7$=OH, $R_8$=OH, $R_9$=O-Lactyl);

5-acetamido-9-O-phosphate-3,5-dideoxy-D-glycero-D-galacto-nonulosonic acid (Neu5Ac9$PO_4$) ($R_5$=NH-Acetyl, $R_7$=OH, $R_8$=OH, $R_9$=O-Phosphate);

5-hydroxyacetamido-9-O-phosphate-3,5-dideoxy-D-glycero-D-galacto-nonulosonic acid (Neu5Gc9$PO_4$) ($R_5$=NH-Glycolyl, $R_7$=OH, $R_8$=OH, $R_9$=O-Phosphate);

5-acetamido-9-O-sulfate-3,5-dideoxy-D-glycero-D-galacto-nonulosonic acid (Neu5Ac9$SO_4$) ($R_5$=NH-Acetyl, $R_7$=OH, $R_8$=OH, $R_9$=O-Sulfate);

5-hydroxyacetamido-9-O-sulfate-3,5-dideoxy-D-glycero-D-galacto-nonulosonic acid (Neu5Gc9$SO_4$) ($R_5$=NH-Glycolyl, $R_7$=OH, $R_8$=OH, $R_9$=O-Sulfate);

5-acetamido-8-O-sulfate-3,5-dideoxy-D-glycero-D-galacto-nonulosonic acid (Neu5Ac8$SO_4$) ($R_5$=NH-Acetyl, $R_7$=OH, $R_8$=O-Sulfate, $R_9$=OH);

5-hydroxyacetamido-8-O-sulfate-3,5-dideoxy-D-glycero-D-galacto-nonulosonic acid (Neu5Gc8$SO_4$) ($R_5$=NH-Glycolyl, $R_7$=OH, $R_8$=O-Sulfate, $R_9$=OH);

5-acetamido-8-O-acetyl-3,5-dideoxy-D-glycero-D-galacto-nonulosonic acid (Neu5Ac8Ac) ($R_5$=NH-Acetyl, $R_7$=OH, $R_8$=O-Acetyl, $R_9$=OH);

5-hydroxyacetamido-8-O-acetyl-3,5-dideoxy-D-glycero-D-galacto-nonulosonic acid (Neu5Gc8Ac) ($R_5$=NH-Glycolyl, $R_7$=OH, $R_8$=O-Acetyl, $R_9$=OH);

5-acetamido-9-amino-3,5,9-trideoxy-D-glycero-D-galacto-nonulosonic acid (Neu5Ac9N) ($R_5$=NH-Acetyl, $R_7$=OH, $R_8$=OH, $R_9$=$NH_2$) or pharmaceutically acceptable salts or derivatives thereof.

In other embodiments, the cytidine 5'-monophospho-nonulosonate sugar may be, but are not necessarily limited to CMP-nonulosonate (CMP-NulO) sugars, where the nonulosonates are selected from:

5,7-diacetamido-3,5,7,9-tetradeoxy-D-glycero-D-galacto-nonulosonic acid (Leg5Ac7Ac);

5-acetamido-9-azido-3,5,9-trideoxy-D-glycero-D-galacto-nonulosonic acid (Neu5Ac9Az);

5-acetamido-9-O-acetyl-3,5-dideoxy-D-glycero-D-galacto-nonulosonic acid (Neu5Ac9Ac);

5-hydroxyacetamido-8-O-methyl-3,5-dideoxy-D-glycero-D-galacto-nonulosonic acid (Neu5Gc8Me); or pharmaceutically acceptable salts or derivatives thereof.

According to a yet further aspect of the invention, there is provided a method for treating or preventing a *N. gonorrhoeae* infection in an individual in need of such treatment comprising administering to said individual an effective amount of a cytidine 5'-monophospho-nonulosonate sugar of Formula (I) or a pharmaceutically acceptable salt or derivative thereof.

The cytidine 5'-monophospho-nonulosonate sugar may be a cytidine 5'-monophospho-nonulosonate sugar of Formula (I):

(I)

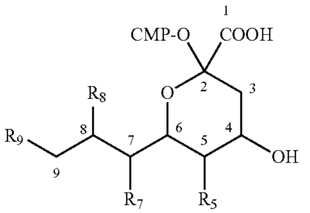

wherein:

$R_5$ is: OH, O-Acetyl, O-Methyl, $NH_2$, NH-Acetyl, NH-Glycolyl, NH-Prop, NH-But, NH-Pent, NH-Hex, NH-Hept, NH-Lev, NH—(O-Acetyl)glycolyl, NH—(O-Methyl)glycolyl, NH—(O-α2Neu5Gc)glycolyl, NH—(N-Methyl)acetimidoyl, NH-(di-N-Methyl)acetimidoyl, NH-(Glutam-4-yl) amino, NH—(N-Methyl-glutam-4-yl)amino, or NH-Azido-acetyl;

$R_7$ is: OH, $NH_2$, O-Acetyl, O-Methyl, O-Lactyl, NH-Acetyl, NH-Azido-acetyl, NH-(D-Alanyl), or NH—(N-Acetyl-D-alanyl);

$R_8$ is: OH, $NH_2$, $N_3$, O-Acetyl, O-Methyl, O-Lactyl, O-Sulfate, O-Sia, or O-Glc; and $R_9$ is: OH, O-Acetyl, $N_3$, $NH_2$, NH-Acetyl, NH-Thioacetyl, Benzamido [NHCOPh], NH-Gly, NH-Succ, $SCH_3$, $SO_2CH_3$, Hexanoylamido [$NHCO(CH_2)_4CH_3$], O-Methyl, O-Lactyl, O-Phosphate, O-Sulfate, O-Sia, or H.

In other embodiments:

$R_5$ is: OH, NH-Acetyl, or NH-Glycolyl;

$R_7$ is: OH, O-Acetyl, O-Methyl, or NH-Acetyl;

$R_8$ is: OH, $NH_2$, $N_3$, O-Acetyl, O-Methyl, or O-Sulfate; and $R_9$ is: OH, O-Acetyl, $N_3$, $NH_2$, O-Methyl, O-Lactyl, O-Phosphate, O-Sulfate, or H.

In yet other embodiments:

$R_5$ is: NH-Acetyl or NH-Glycolyl;

$R_7$ is: OH or NH-Acetyl;

$R_8$ is: OH or O-Methyl; and $R_9$ is: OH, O-Acetyl, $N_3$, or H.

In other embodiments, the compounds of the present invention may be, but are not necessarily limited to CMP-nonulosonate (CMP-NulO) sugars, where the nonulosonates are selected from:

5,7-diacetamido-3,5,7,9-tetradeoxy-D-glycero-D-galacto-nonulosonic acid (Leg5Ac7Ac) ($R_5$=NH-Acetyl, $R_7$=NH-Acetyl, $R_8$=OH, $R_9$=H);

5,7-diacetamido-9-azido-3,5,7,9-tetradeoxy-D-glycero-D-galacto-nonulosonic acid (Leg5Ac7Ac9Az) ($R_5$=NH-Acetyl, $R_7$=NH-Acetyl, $R_8$=OH, $R_9$=$N_3$);

5,7-diacetamido-8-amino-3,5,7,8,9-pentadeoxy-D-glycero-D-galacto-nonulosonic acid (Leg5Ac7Ac8N) ($R_5$=NH-Acetyl, $R_7$=NH-Acetyl, $R_8$=$NH_2$, $R_9$=H);

5-acetamido-9-azido-3,5,9-trideoxy-D-glycero-D-galacto-nonulosonic acid (Neu5Ac9Az) ($R_5$=NH-Acetyl, $R_7$=OH, $R_8$=OH, $R_9$=$N_3$);

5-hydroxyacetamido-9-azido-3,5,9-trideoxy-D-glycero-D-galacto-nonulosonic acid (Neu5Gc9Az) ($R_5$=NH-Glycolyl, $R_7$=OH, $R_8$=OH, $R_9$=$N_3$);

5-acetamido-9-O-acetyl-3,5-dideoxy-D-glycero-D-galacto-nonulosonic acid (Neu5Ac9Ac) ($R_5$=NH-Acetyl, $R_7$=OH, $R_8$=OH, $R_9$=O-Acetyl);

5-hydroxyacetamido-9-O-acetyl-3,5-dideoxy-D-glycero-D-galacto-nonulosonic acid (Neu5Gc9Ac) ($R_5$=NH-Glycolyl, $R_7$=OH, $R_8$=OH, $R_9$=O-Acetyl);

2-keto-3-deoxy-9-O-acetyl-D-glycero-D-galacto-nonulosonic acid (Kdn9Ac) ($R_5$=OH, $R_7$=OH, $R_8$=OH, $R_9$=O-Acetyl);

5-acetamido-8-O-methyl-3,5-dideoxy-D-glycero-D-galacto-nonulosonic acid (Neu5Ac8Me) ($R_5$=NH-Acetyl, $R_7$=OH, $R_8$=O-Methyl, $R_9$=OH);

5-hydroxyacetamido-8-O-methyl-3,5-dideoxy-D-glycero-D-galacto-nonulosonic acid (Neu5Gc8Me) ($R_5$=NH-Glycolyl, $R_7$=OH, $R_8$=O-Methyl, $R_9$=OH);

5-acetamido-9-O-methyl-3,5-dideoxy-D-glycero-D-galacto-nonulosonic acid (Neu5Ac9Me) ($R_5$=NH-Acetyl, $R_7$=OH, $R_8$=OH, $R_9$=O-Methyl);

5-hydroxyacetamido-9-O-methyl-3,5-dideoxy-D-glycero-D-galacto-nonuloson is acid (Neu5Gc9Me) ($R_5$=NH-Glycolyl, $R_7$=OH, $R_8$=OH, $R_9$=O-Methyl);

2-keto-3-deoxy-9-O-methyl-D-glycero-D-galacto-nonulosonic acid (Kdn9Me) ($R_5$=OH, $R_7$=OH, $R_8$=OH, $R_9$=O-Methyl);

5-acetamido-9-O-lactyl-3,5-dideoxy-D-glycero-D-galacto-nonulosonic acid (Neu5Ac9Lt) ($R_5$=NH-Acetyl, $R_7$=OH, $R_8$=OH, $R_9$=O-Lactyl);

5-hydroxyacetamido-9-O-lactyl-3,5-dideoxy-D-glycero-D-galacto-nonulosonic acid (Neu5Gc9Lt) ($R_5$=NH-Glycolyl, $R_7$=OH, $R_8$=OH, $R_9$=O-Lactyl);

5-acetamido-9-O-phosphate-3,5-dideoxy-D-glycero-D-galacto-nonulosonic acid (Neu5Ac9$PO_4$) ($R_5$=NH-Acetyl, $R_7$=OH, $R_8$=OH, $R_9$=O-Phosphate);

5-hydroxyacetamido-9-O-phosphate-3,5-dideoxy-D-glycero-D-galacto-nonulosonic acid (Neu5Gc9$PO_4$) ($R_5$=NH-Glycolyl, $R_7$=OH, $R_8$=OH, $R_9$=O-Phosphate);

5-acetamido-9-O-sulfate-3,5-dideoxy-D-glycero-D-galacto-nonulosonic acid (Neu5Ac9$SO_4$) ($R_5$=NH-Acetyl, $R_7$=OH, $R_8$=OH, $R_9$=O-Sulfate);

5-hydroxyacetamido-9-O-sulfate-3,5-dideoxy-D-glycero-D-galacto-nonulosonic acid (Neu5Gc9$SO_4$) ($R_5$=NH-Glycolyl, $R_7$=OH, $R_8$=OH, $R_9$=O-Sulfate);

5-acetamido-8-O-sulfate-3,5-dideoxy-D-glycero-D-galacto-nonulosonic acid (Neu5Ac8$SO_4$) ($R_5$=NH-Acetyl, $R_7$=OH, $R_8$=O-Sulfate, $R_9$=OH);

5-hydroxyacetamido-8-O-sulfate-3,5-dideoxy-D-glycero-D-galacto-nonulosonic acid (Neu5Gc8$SO_4$) ($R_5$=NH-Glycolyl, $R_7$=OH, $R_8$=O-Sulfate, $R_9$=OH);

5-acetamido-8-O-acetyl-3,5-dideoxy-D-glycero-D-galacto-nonulosonic acid (Neu5Ac8Ac) ($R_5$=NH-Acetyl, $R_7$=OH, $R_8$=O-Acetyl, $R_9$=OH);

5-hydroxyacetamido-8-O-acetyl-3,5-dideoxy-D-glycero-D-galacto-nonulosonic acid (Neu5Gc8Ac) ($R_5$=NH-Glycolyl, $R_7$=OH, $R_8$=O-Acetyl, $R_9$=OH);

5-acetamido-9-amino-3,5,9-trideoxy-D-glycero-D-galacto-nonulosonic acid (Neu5Ac9N) ($R_5$=NH-Acetyl, $R_7$=OH, $R_8$=OH, $R_9$=$NH_2$) or pharmaceutically acceptable salts or derivatives thereof.

In other embodiments, the cytidine 5'-monophospho-nonulosonate sugar may be, but are not necessarily limited to CMP-nonulosonate (CMP-NulO) sugars, where the nonulosonates are selected from:

5,7-diacetamido-3,5,7,9-tetradeoxy-D-glycero-D-galacto-nonulosonic acid (Leg5Ac7Ac);

5-acetamido-9-azido-3,5,9-trideoxy-D-glycero-D-galacto-nonulosonic acid (Neu5Ac9Az);

5-acetamido-9-O-acetyl-3,5-dideoxy-D-glycero-D-galacto-nonulosonic acid (Neu5Ac9Ac);

5-hydroxyacetamido-8-O-methyl-3,5-dideoxy-D-glycero-D-galacto-nonuloson is acid (Neu5Gc8Me); or pharmaceutically acceptable salts or derivatives thereof.

According to another aspect of the invention, there is provided a method for identifying a cytidine 5'-monophospho-nonulosonate sugar capable of reducing virulence of *N. gonorrhoeae* comprising: incubating *N. gonorrhoeae* with the cytidine 5'-monophospho-nonulosonate sugar of interest under conditions suitable for incorporation of nonulosonate sugar into lipooligosaccharide of the *N. gonorrhoeae; and determining if serum resistance of the N. gonorrhoeae* is reduced compared to an untreated control culture of *N. gonorrhoeae.*

As will be apparent to one of skill in the art, incubation of any suitable cytidine 5'-monophospho-nonulosonate sugar that is a substrate for Lst will result in incorporation of nonulosonate sugar into lipooligosaccharide of the *N. gonorrhoeae. The serum resistance of the N. gonorrhoeae* with the modified LOS can then be tested as discussed herein, as well as measurement of factor H binding, IgG binding or C4 deposition.

In some embodiments, the incubation may be carried out in the presence of CMP-Neu5Ac. As discussed above, in these embodiments, it can be determined if the 5'-monophospho-nonulosonate sugar of interest can out-compete CMP-Neu5Ac.

The 5'-monophospho-nonulosonate sugar of interest identified according to the method described above can then be used to treat or prevent a *N. gonorrhoeae* infection, as discussed above.

According to a further aspect of the invention, there is provided a method for treating or preventing a *N. gonorrhoeae* infection in an individual in need of such treatment comprising:

identifying a cytidine 5'-monophospho-nonulosonate sugar capable of reducing virulence of *N. gonorrhoeae* by incubating *N. gonorrhoeae* with the cytidine 5'-monophospho-nonulosonate sugar of interest under conditions suitable for incorporation of the nonulosonate sugar of interest into lipooligosaccharide of the *N. gonorrhoeae*; and determining if serum resistance of the *N. gonorrhoeae* is reduced compared to an untreated control culture of *N. gonorrhoeae*; and if said cytidine 5'-monophospho-nonulosonate sugar reduces the serum resistance, administering an effective amount of said cytidine 5'-monophospho-nonulosonate sugar to said individual.

Described herein is the substrate specificity of gonococcal LOS sialyltransferase Lst in the context of intact bacteria and the structural requirements for sialic acid necessary to facilitate fH binding to, and complement resistance of *N. gonorrhoeae*. Table 1 provides a summary of these results. Substitutions at carbon 7 (evidenced by Leg5Ac7Ac), carbon 8 (Neu5Gc8Me) and carbon 9 (Neu5Ac9Ac and Neu5Ac9Az) positions all adversely affect high-level serum resistance conferred by the 'physiologic' gonococcal LOS sialic acid, Neu5Ac. These data also suggest that the negative charge of sialic acids alone is not sufficient for fH binding—Neu5Gc8Me, Leg5Ac7Ac and Neu5Ac9Az are all negatively charged, yet do not enhance fH binding. In contrast, N-glycolyl substitution at the 5-position did not have any negative impact on fH binding or serum resistance. The importance of the carbon 9 substitution reported here are in accordance with a prior study by Michalek and colleagues, who showed that chemical modification to remove the 9 carbon was associated with loss of 90% of the complement inhibition by sialic acid (26). The lack of an effect on alternative pathway when the 5Ac group is replaced with 5Gc is also consistent with the prior study (26).

The inventors have previously reported classical pathway regulation with sialylation of gonococcal LOS (15). In assays that were performed using relatively high numbers of bacteria (~$10^8$ CFU) relative to serum amount and concentration (10 μl in a final volume of 100 μl), no differences in IgG binding were observed when LOS was sialylated (15). In the context of the current invention, reducing the number of bacteria in the complement binding assays to better simulate conditions in serum bactericidal assays revealed a substantial reduction in binding of IgG to sialylated bacteria. Reduced IgG binding could account, at least in part, for classical pathway regulation mediated by Neu5Ac. Two optimally spaced Fc domains of complement-fixing IgG subclasses can engage a C1 complex to initiate classical pathway activation. An arithmetic increase in the number of IgG molecules bound results in a geometric increase in the number of 'suitable pairs' of Fc domains to initiate the classical pathway. Thus, relatively small changes in IgG binding lead to disproportionately greater differences in C4 fragment deposition and downstream complement activation. Of note, Neu5Ac also caused a small but reproducible reduction in IgM binding. On a molar basis, IgM is more effective in activating the classical pathway because a single IgM molecule can engage the C1 complex to trigger the classical pathway. It is possible that the small decrease in IgM binding seen with Neu5Ac LOS substitution also contributes to complement inhibition. The 8Me and 9Ac substitutions also markedly reduced IgG binding, but did not appreciably decrease IgM binding. Downstream events, including C4, C3 and factor B deposition (the latter a measure of alternative pathway recruitment), were effectively regulated only in low serum concentrations, but likely did not reach a threshold that permitted bacterial survival in 10% complement.

LOS is a target for C4 and C3 fragment deposition on *Neisseria* (27); sialylation of the terminal Gal residue could contribute to complement regulation by obscuring targets for C3 and C4. Binding of fH hastens dissociation of alternative pathway C3/C5 convertases (C3b,Bb and C3bC3b,Bb, respectively) (28) and likely contributes to the barely detectable levels of factor B on the Neu5Ac-bearing strain even in 10% serum.

Figure 5:
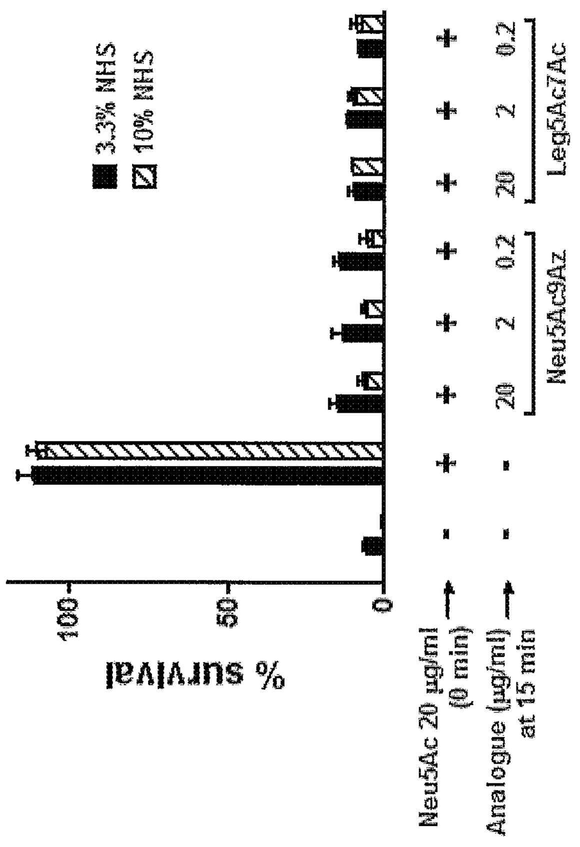
FIG. 5. CMP-Neu5Ac9Az and CMP-Leg5Ac7Ac can counteract serum resistance mediated by CMP-Neu5Ac. *N. gonorrhoeae* F62 ΔlgtD was suspended in media containing 20 μg/ml (~30 μM) CMP-Neu5Ac. Following 15 min of incubation at 37° C., CMP-Neu5Ac9Az or CMP-Leg5Ac7Ac (at concentrations of 20, 2 or 0.2 μg/ml final) were added and bacteria were incubated for 2 h. Serum bactericidal assays were then performed using 3.3% (solid black bars) or 10% (hatched bars) NHS. Controls included bacteria in media that lacked any CMP-nonulosonate, or bacteria that were incubated in CMP-Neu5Ac only. Y-axis, % survival. The mean (SD) of two independent experiments is shown.

Herein, it has been shown that select analogues of nonulosonic acids, such as Neu5Ac9Az and Leg5Ac7Ac can block Neu5Ac-mediated serum resistance (FIG. 5). In vitro, the effects of these CMP-nonulosonate analogues are evident when added to bacteria within a short period of adding CMP-Neu5Ac. However, bacteria in vivo actively replicate and are likely to incorporate the competing nonulosonate analogue over time, instead of Neu5Ac. A rather surprising finding was that the effects of CMP-Neu5Ac were negated even when CMP-Neu5Ac9Az or CMP-Leg5Ac7Ac were provided at ~100-fold lower concentrations. This suggests that even minimal incorporation of Neu5Ac9Az or Leg5Ac7Ac relative to Neu5Ac incorporation can turn a normally serum-resistant *N. gonorrhoeae* cell into a serum-sensitive *N. gonorrhoeae* cell. As will be appreciated by one of skill in the art, this indicates that any of a variety of CMP-nonulosonate sugars described herein can be used to reduce virulence of *N. gonorrhoeae*, that is, to treat a *N. gonorrhoeae* infection, as described herein.

Of the two competing analogues studies, CMP-Leg5Ac7Ac showed the least amount of complement inhibition. While the competing nonoses did not affect fH binding that was facilitated by Neu5Ac, they interfered with classical pathway inhibition (measured by IgG binding and C4 deposition) by Neu5Ac and were able to block serum resistance. This finding, coupled with the observation that serum resistance of sialylated gonococci lags behind their ability to bind to fH (both measured as a function of the time of exposure to CMP-Neu5Ac), demonstrates that evasion of the classical pathway is required for high level complement resistance.

These findings have shed fresh light on the molecular basis of gonococcal LOS sialylation and how this translates to complement regulation on the bacterial surface. The identification of CMP-nonulosonic acid analogues that can interfere with a key virulence mechanism of *N. gonorrhoeae* paves the way to develop novel therapeutic strategies against rapidly spreading multi-drug resistant gonococcal infections.

Also described herein is the use of Neisserial Lst sialyltransferases to modify glycans, for example N- and O-linked glycans, with legionaminic acid, specifically, modifying N-acetyl-D-lactosamine (LacNAc) residues. Without being limiting in scope, this modification may increase the biological half-life of the respective glycoconjugate.

The enzyme family is the only one that is able to efficiently modify LacNAc with legionaminic acid using a CMP-Leg5Ac7Ac donor.

Accordingly, there is provided a process for modifying a molecule with N,N'-diacetyllegionaminic acid (Leg5Ac7Ac) comprising: contacting an acceptor molecule bearing a terminal Galβ-1,4-GlcNAc (LacNAc) residue with an activated sugar nucleotide of N,N'-diacetyllegionaminic acid (e.g. cytidine 5'-monophospho-N,N'-(diacetyllegionaminic acid or CMP-Leg5Ac7Ac) in the presence of a sialyltransferase derived from a *Neisseria* spp. (especially *N. gonorrhoeae* or *N. meningitidis*).

This enzyme family is the only one able to efficiently modify LacNAc residues with Leg5Ac7Ac (near 100% product conversion), as to date no others have been reported to do so. In addition, as seen in FIG. 11, this enzyme family is highly specific for LacNAc acceptors since Lacto-N-biose, TAg, and Pk acceptors were not utilized when CMP-Leg5Ac7Ac was the donor, whereas all but TAg could be efficiently utilized using CMP-Neu5Ac donor. Furthermore, Neisserial Lst can remove Neu5Ac from modified LacNAc acceptors over time, whereas this was not observed with Leg5Ac7Ac modified LacNAc (FIG. 11, lanes 1 versus 5), suggesting greater stability of Leg5Ac7Ac enzymatic products. Importantly, previous work by Watson et al. (39) has shown that glycoconjugates containing Leg5Ac7Ac as a replacement for Neu5Ac are sialidase resistant and therefore expected to have increased biological half-lives. This increase in half-life would be beneficial for many non-antibody biologic therapeutics such as erythropoietin and Factor VIII, who suffer from sub-optimal half-life largely due to removal of sialic acids from their glycoconjugates. By replacing Neu5Ac with Leg5Ac7Ac in these molecules, the sub-terminal Gal residues that are recognized by the hepatic Aswell-Morell receptors causing clearance would remain 'masked'. Also, Watson et al. (39) did not find sialyltransferases capable of modifying LacNAc residues with Leg5Ac7Ac, only ones that modify Lac (Galβ-1,4-GlcNAcβ) and T-antigen (Galβ-1,3-GalNAcα) structures. Surprisingly, these authors (39) found *N. meningitidis* Lst incapable of modifying LacNAc with Leg5Ac7Ac, but it is shown here that *N. gonorrhoeae* Lst efficiently modifies LacNAc with Leg5Ac7Ac (FIG. 11), and we have also observed similar results with *N. meningitidis* Lst enzymes. The process involves an acceptor molecule (i.e. the LacNAc-bearing macromolecule) and a Leg5Ac7Ac donor molecule that takes the form of an activated sugar nucleotide (e.g. CMP-Leg5Ac7Ac, where CMP is cytidine 5'-monophosphate).

Results

Substrate Specificity of Gonococcal Lipooligosaccharide Sialyltransferase

To define the substrate specificity of gonococcal LOS sialyltransferase, *N. gonorrhoeae* F62 ΔIgtD was grown in media alone, or media that contained the CMP-activated derivatives of 7 nonulosonates (listed in Table 1), each at a concentration of 30 μM (20 μg/ml). Following incubation for 2 h at 37° C., bacteria were washed, lysed with protease K/LDS sample buffer and separated on 12% Bis-tris gels. Blots were probed with mAb 3F11, which binds to the terminal lactosamine residue of lacto-N-neotetraose (LNT); any extension beyond the terminal Gal (in this instance with a nonose) would abrogate 3F11 binding. As shown in FIG. 1 (upper panel), growth in media containing CMP salts of Neu5Ac, Neu5Gc, Neu5Ac9Ac, Neu5Ac9Az, Neu5Gc8Me and Leg5Ac7Ac all decreased binding of mAb 3F11, suggesting that these CMP-nonulosonates served as substrates for gonococcal Lst in the context of live bacteria and the respective nonulosonates were incorporated onto LNT. The only nonulosonate not incorporated in LNT LOS was Pse5Ac7Ac. Consistent with loss of 3F11 binding and addition of a nonose residue, silver staining of LOS showed a slight retardation in mobility of the 6 lanes that showed decreased mAb 3F11 binding relative to the migration of bacterial samples that bound mAb 3F11 (FIG. 1, middle panel). Whole cell ELISA with mAb 3F11 confirmed results of western blotting (FIG. 1, lower graph).

Serum Resistance Mediated by Incorporation of Nonulosonates

Figure 8:
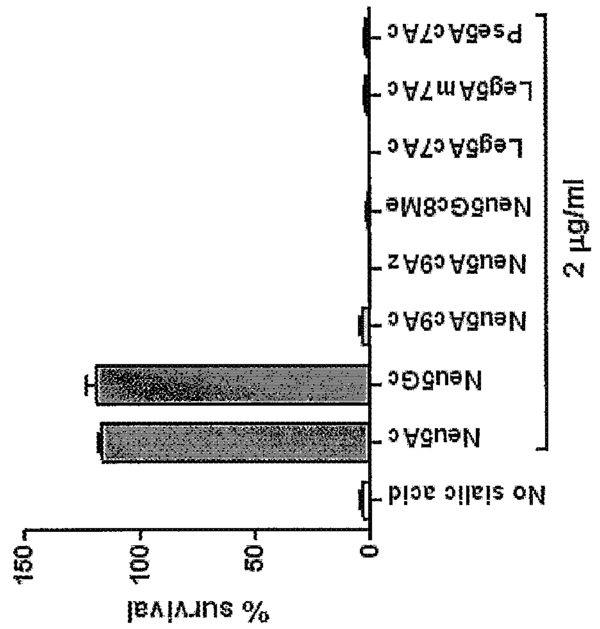
FIG. 8. Effect of CMP-nonulosonic acid analogues on the resistance of *N. gonorrhoeae* to complement-dependent killing. *N. gonorrhoeae* F62 ΔlgtD was grown in media alone, or in media containing 2 μg/ml (~3 μM) of each of the indicated CMP-nonulosonates. Resistance to killing by 10% NHS was measured in a serum bactericidal assay. Y-axis, % survival. The mean (SD) of two independent experiments is shown. CMP-Leg5Am7Ac, like CMP-Pse5Ac7Ac, is an analogue that was not utilized by the *N. gonorrhoeae* Lst sialyltransferase.

Addition of a terminal Neu5Ac residue to the LNT LOS of *N. gonorrhoeae* that occurs in vivo or following the addition of CMP-Neu5Ac to growth media results in resistance to complement-dependent killing (17). We next determined the effects of incorporation of the CMP salts of five structural analogues of Neu5Ac (Neu5Gc, Neu5Ac9Ac, Neu5Ac9Az, Neu5Gc8Me and Leg5Ac7Ac) on the ability of *N. gonorrhoeae* F62 ΔIgtD to resist complement-dependent killing by normal human serum at concentrations of 10, 6.7 or 3.3%. Bacteria were grown either in media alone, or media supplemented with 30 μM (~20 μg/ml) of each of the CMP-nonulosonates. As shown in FIG. 2, only Neu5Ac (serum-resistant control) and Neu5Gc conferred full (>100%) survival at serum concentrations of 10%. Neu5Ac9Ac and Neu5Gc8Me incorporation conferred >100% survival only in 3.3% serum, but did not protect the bacteria (<10% survival) when serum concentrations were raised to 6.7%. The addition of Neu5Ac9Az and Leg5Ac7Ac to LOS did not increase bacterial survival at all serum concentrations tested. As expected, Pse5Ac7Ac was not added onto LOS and did not affect serum resistance. Similar results were obtained when CMP-nonulosonate concentrations in growth media were decreased to 3 μM (~2 μg/ml); only CMP-Neu5Ac and CMP-Neu5Gc conferred resistance to 10% serum (FIG. 8).

Figure 3:
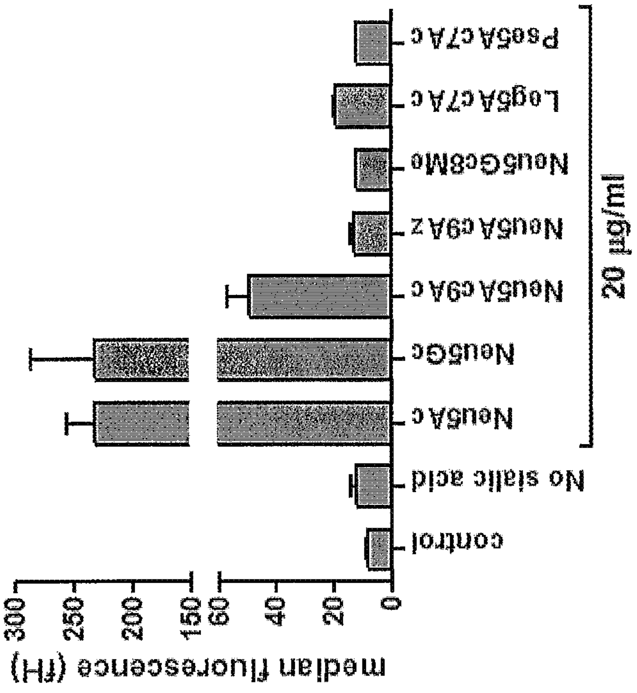
FIG. 3. Effects of LOS modification with various nonulosonate analogues on fH binding to *N. gonorrhoeae. N. gonorrhoeae* F62 ΔlgtD was grown in media alone, or media supplemented with 20 μg/ml (~30 μM) of each of the indicated CMP-nonulosonates. Binding of bacteria to fH (10 μg/ml) was measured by flow cytometry using polyclonal goat anti-human fH. The control indicates reaction mixtures that lacked fH. Y-axis, median fluorescence of fH binding. The mean (SD) of 2 independent repeats is shown.
Figure 9:
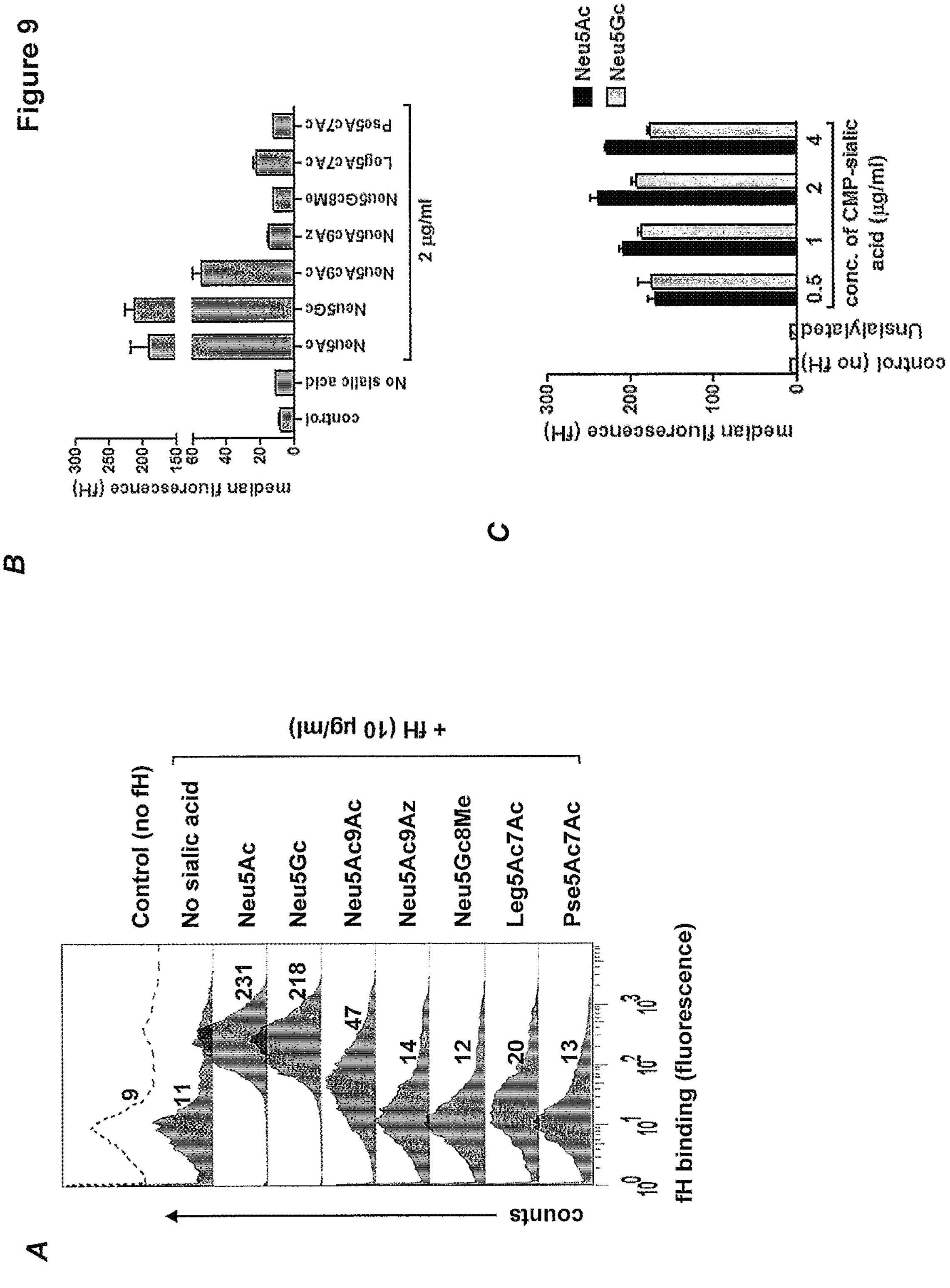
FIG. 9. fH binding to *N. gonorrhoeae* grown in media containing CMP-nonulosonic acid analogues. A. Representative histogram tracings of an experiment depicted in FIG. 3. X-axis, fluorescence (log 10 scale); Y-axis, counts. Numbers alongside each histogram represents the median fluorescence. Control represents bacteria that were incubated in buffer alone (no added fH). B. fH binding to *N. gonorrhoeae*

Factor H Binding and Complement Activation Mediated by Incorporation of Nonulosonates The addition of a terminal Neu5Ac residue to LNT-expressing LOS enhances binding of the alternative pathway inhibitor, factor H, which contributes to the ability of sialylated gonococci to resist killing by complement (7). fH binding to *N. gonorrhoeae* F62 ΔlgtD grown in the presence of each of the CMP-nonulosonates (20 μg/ml or 30 μM) was examined (FIG. 3). Maximal fH binding was seen with Neu5Ac and Neu5Gc, an 'intermediate' level of fH binding was seen with Neu5Ac9Ac, while all the other nonulosonates did not enhance fH binding above levels seen with unsialylated F62 ΔlgtD. Reducing the CMP-nonulosonate concentrations in growth media to 2 μg/ml (3 μM) yielded similar fH binding results (FIG. 9B). Further, modification of LOS with Neu5Ac or Neu5Gc yielded similar amounts of fH binding over CMP-sialic acid concentrations ranging from 0.5 to 4 μg/ml, with near maximal fH binding observed even at the lowest concentration tested (FIG. 9C).

Binding of IgG and IgM to, and deposition of complement components C3, C4 and factor B on *N. gonorrhoeae* F62 ΔlgtD grown in the presence of the following CMP-nonulosonates was examined based on results of bactericidal assays and fH binding. Neu5Ac was used as an example of a nonose that conferred high level resistance and bound high levels of fH, Neu5Ac8Me as a nonose that mediated low level serum resistance with undetectable binding of fH by FACS, Neu5Ac9Ac as a nonose that conferred low levels of serum resistance and showed 'intermediate' levels of fH binding by FACS, and Neu5Ac9Az and Leg5Ac7Ac as nonoses that did not confer serum resistance and did not bind fH. *N. gonorrhoeae* F62 ΔlgtD with an unmodified (unsialylated) LNT LOS was used as the control serum sensitive strain. Experiments were carried out using serum concentrations of 10% and 3.3%, which represented the serum concentrations that produced discriminating phenotypes with Neu5Ac9Ac and Neu5Gc8Me.

Figure 4:
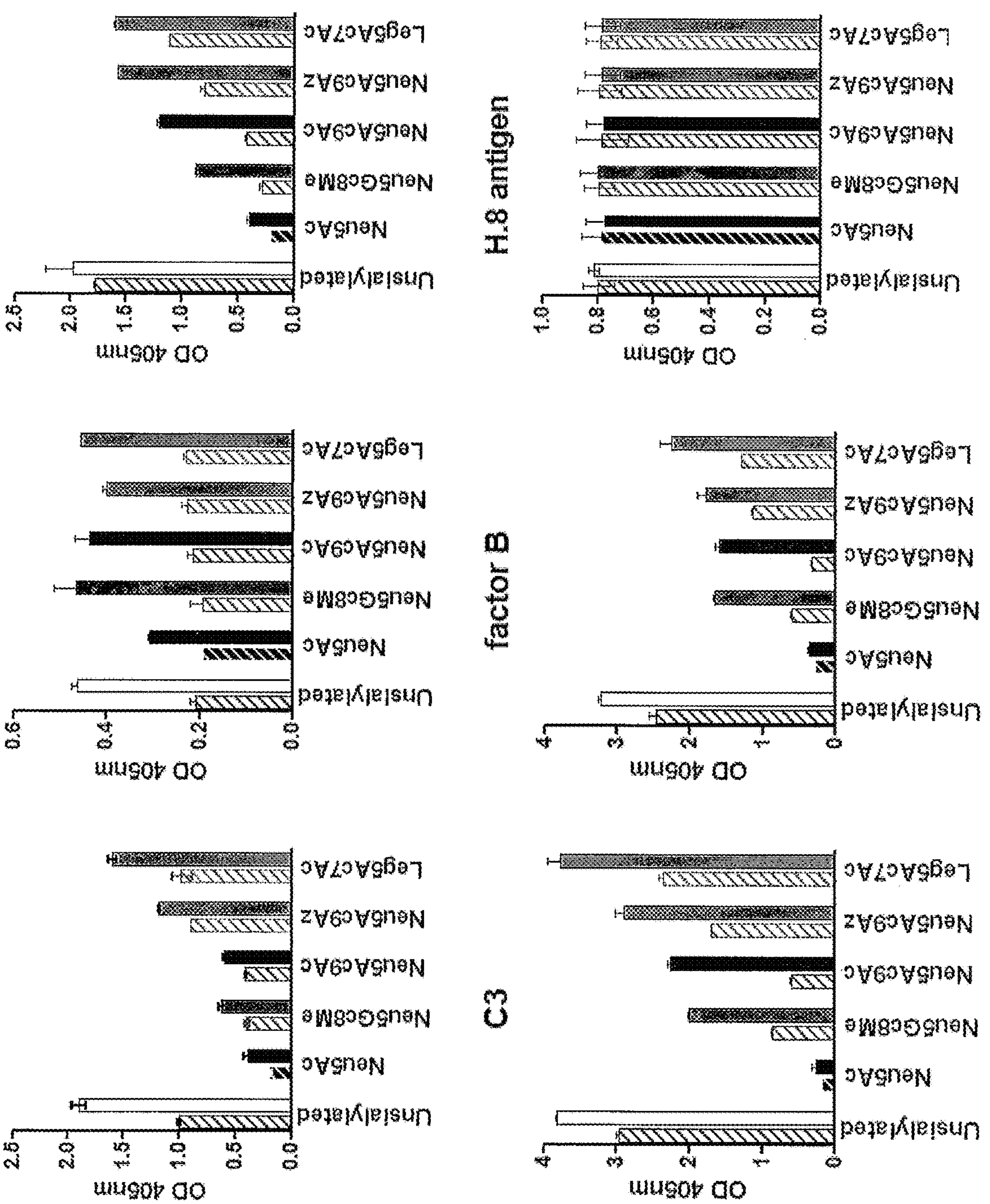
FIG. 4. Complement C3 and C4 deposition on, and factor B binding to *N. gonorrhoeae* bearing nonulosonic acid analogues on LOS. *N. gonorrhoeae* F62 ΔlgtD was grown in media alone (open bars), or media supplemented with 20 μg/ml (~30 μM) of each of the indicated CMP-nonulosonates. Bacteria were incubated with either 3.3% or 10% NHS at 37° C. for 10 min and IgG and IgM binding, and C3, C4 and factor B deposited on bacteria were measured by whole cell ELISA. Data with 3.3% and 10% NHS is shown by hatched and solid bars, respectively. Measurement of gonococcal H.8 lipoprotein antigen was performed to ensure similar bacterial capture to microtiter wells. The mean (SD) of triplicate observations is shown.

As expected, modification with Neu5Ac resulted in maximal complement inhibition (lowest C3, C4 and fB deposition) at both serum concentrations, while high levels of complement activation products were deposited on *N. gonorrhoeae* F62 ΔlgtD (unsialylated) (FIG. 4). LOS substitution with Neu5Ac decreased IgG binding substantially, which could at least in part, contribute to decreased C4 deposition. Further, a small but reproducible decrease in IgM binding was seen only with Neu5Ac substitution. While LOS modification with Neu5Ac9Ac and Neu5Gc8Me (both resistant only to 3.3%, but not 10%, serum) yielded low levels of C3, C4 and factor B deposition that reflected their serum resistant phenotype in 3.3% serum, only a modest decline in deposition of these components was noted in 10% serum when compared with F62 ΔlgtD (unsialylated) that likely was insufficient to subvert killing by complement. Neu5Gc8Me and Neu5Ac9Ac substitution also reduced IgG binding, but not to the extent seen with Neu5Gc. The two analogues that left *N. gonorrhoeae* F62 ΔlgtD fully serum sensitive, Neu5Ac9Az and Leg5Ac7Ac, yielded the highest levels of complement deposition and Ig binding among the tested analogues.

Select Nonulosonate Derivatives Inhibit Neu5Ac-Mediated Serum Resistance

The ability of two of the CMP-nonulosonates, CMP-Neu5Ac9Az and CMP-Leg5Ac7Ac, to counter the ability of CMP-Neu5Ac to enhance serum resistance of *N. gonorrhoeae* was then examined. The analogues were added at concentrations of 20, 2 or 0.2 μg/ml to growth media 15 min after the addition of CMP-Neu5Ac (20 μg/ml) to F62 ΔlgtD. As shown in FIG. 5, both CMP-Neu5Ac9Az and CMP-Leg5Ac7Ac blocked serum resistance mediated by CMP-Neu5Ac, even when the latter was present at a 100-fold molar excess. As expected, bacteria remained serum sensitive when the competing nonulosonate was added to media at the same time as CMP-Neu5Ac. However, addition of CMP-Neu5Ac9Az and CMP-Leg5Ac7Ac to media 120 min after the addition of CMP-Neu5Ac which allows for the development of full (>100% survival) serum resistance (18), did not induce any killing (data not shown).

Competing Nonulosonate Analogues Permit Unimpeded Classical Activation, but do not Affect fH Binding To define the mechanism whereby Neu5Ac9Az and Leg5Ac7Ac blocked complement resistance by Neu5Ac, we studied Ab binding to, and complement component deposition on *N. gonorrhoeae* F62 ΔlgtD that was incubated with CMP-Neu5Ac (20 μg/ml), followed 15 min later with either CMP-Neu5Ac9Az or CMP-Leg5Ac7Ac at concentrations of 20, 2 or 0.2 μg/ml. Controls included bacteria grown in the absence of any CMP-nonulosonate, or bacteria grown in CMP-Neu5Ac alone.

As shown in FIG. 6, incorporation of Neu5Ac onto LOS decreased IgG binding and deposition of complement components C4, C3 and factor Bb. However, addition of Neu5Ac9Az or Leg5Ac7Ac at all concentrations tested blocked this decrease in IgG binding and complement deposition. Similar results were seen with 3.3% NHS (FIG. 10), as was seen with 10% NHS (FIG. 6).

Figure 7:
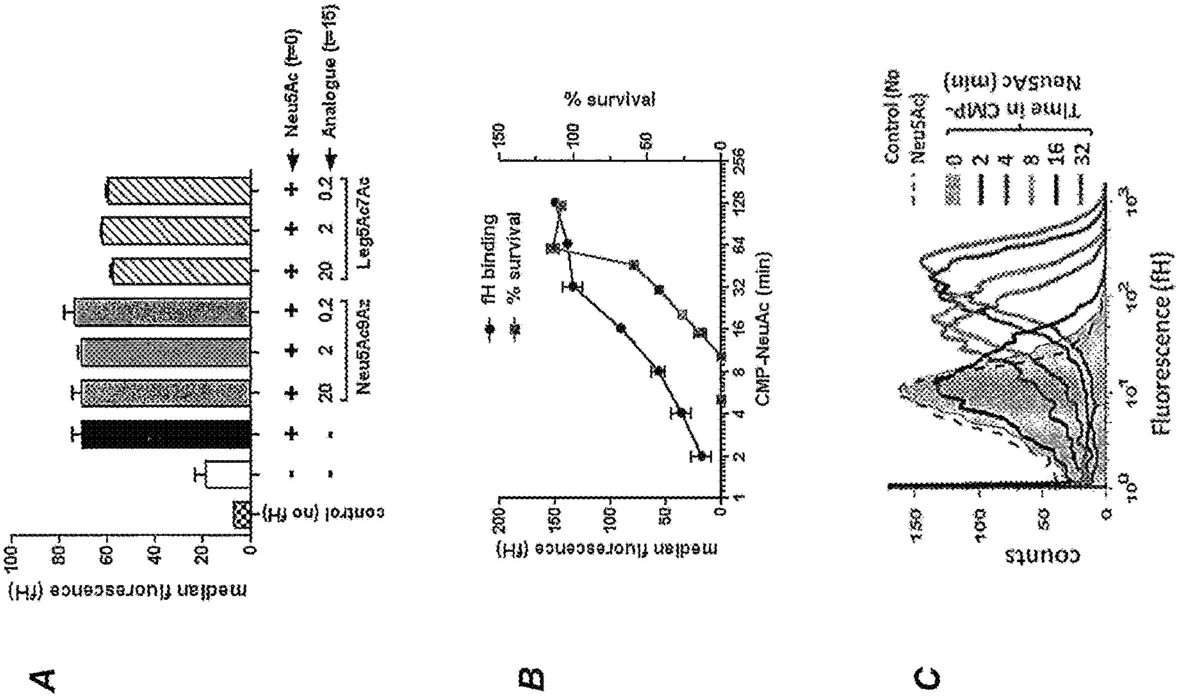
FIG. 7. CMP-Neu5Ac9Az and CMP-Leg5Ac7Ac do not block CMP-Neu5Ac mediated enhancement of fH binding. A. *N. gonorrhoeae* F62 ΔlgtD was incubated in media containing CMP-Neu5Ac (20 μg/ml), followed within 2 min by the addition of either CMP-Neu5Ac9Az or CMP-Leg5Ac7Ac (20, 2 or 0.2 μg/ml). Bacteria were grown for 2 h and fH binding detected by FACS using polyclonal goat anti-human fH. The Y-axis represents median fluorescence. The mean (SEM) of two independent observations is shown. B. Development of serum resistance lags behind fH binding when measured as a function of time of exposure of bacteria to CMP-Neu5Ac. CMP-Neu5Ac (20 μg/ml) was added to media containing F62 ΔlgtD and bacteria were taken at the time points indicated on the X-axis and assayed for fH binding by FACS with anti-fH mAb 90× (left Y-axis; median fluorescence (SEM)), or tested for its ability to resist killing by 10% NHS (right Y-axis; percent survival). The data represent 2-3 independent experiments. C. Representative histograms of a fH binding FACS experiment.

Rather surprisingly, adding CMP-Neu5Ac9Az or CMP-Leg5Ac7Ac even within 2 min of incubation with CMP-Neu5Ac did not interfere with fH binding to *N. gonorrhoeae* F62 ΔlgtD (FIG. 7A). Thus, blocking of Neu5Ac-dependent serum resistance by these analogues was not the result of inhibiting fH binding. The kinetics of fH binding and serum resistance mediated by CMP-Neu5Ac were studied and revealed a lag between fH binding and serum resistance (FIGS. 7B and 7C)—barely any fH binding above control levels was seen at 2 min, while ~70% of maximal binding occurred by 16 min and near maximal binding was achieved by 32 min, bacterial survival at this time point was only ~42%. Collectively, these data suggest that fH binding to bacteria alone was not sufficient for full serum resistance; inhibition of the classical pathway also plays a key role in the serum resistance mediated by gonococcal LOS LNT Neu5Ac.

Based on the results above, CMP-Neu5Ac9Az and CMP-Leg5Ac7Ac were studied further. We next asked if Leg5Ac7Ac and Neu5Ac9Az could block serum resistance mediated by Neu5Ac in the antibiotic resistant 'superbug' H041 (FIG. 12). Ng F62 ΔlgtD and antibiotic resistant 'superbug' H041 (52) were grown in media containing CMP-Neu5Ac (20 μg/ml). CMP-Neu5Ac9Az or CMP-Leg5Ac7Ac (at 0.2, 2 and 20 μg/ml) were added 15 min after CMP-Neu5Ac, and Ng were grown for an additional 2 h. Neu5Ac-mediated serum resistance of F62 ΔlgtD was completely blocked by all tested concentrations of the competing CMP-NulOs, while the serum resistance of H041 (intrinsically more resistant to complement than F62) was countered (<20% survival) by 20 μg/ml (~30 μM) of CMP-NulOs.

The efficacy of CMP-Leg5Ac7Ac against Ng was tested in the BALB/c vaginal colonization model (FIG. 13) (51). Three groups of 17β-estradiol treated BALB/c mice (10 mice/group) were infected as follows: i) WT F62→CMP-Leg5Ac7Ac (10 μg intravaginally daily), ii) WT F62→saline control ('untreated') and iii) F62 List (cannot sialylate LOS)→untreated. Treatment with CMP-Leg5Ac7Ac significantly attenuated Ng infection, similar to that seen with the List mutant (FIGS. 13A and 13B). Importantly, we showed that bacteria recovered directly (i.e., without sub-passage) from CMP-Leg5Ac7Ac-treated mice became sensitive to human complement (not shown), thus recapitulating findings in vitro. Similarly, colonization of mice with the H041 'superbug' was also attenuated by CMP-Leg5Ac7Ac treatment (FIGS. 13C and 13D).

CMP-Leg5Ac7Ac and CMP-Neu5Ac9Az also counteracted CMP-Neu5Ac-mediated serum resistance of a $P^K$ LOS expressing isolate called 398078 (Table 4).

As will be well known to those knowledgeable in the art, the majority of *N. gonorrhoeae* strains have at least some LNT LOS whereas only a few strains have $P^k$ LOS only. However, this data confirms that the methods of the invention are effective against all strains of *N. gonorrhoeae.*

The acceptor specificity of *N. gonorrhoeae* Lst sialyltransferase was assessed using CMP-Neu5Ac and CMP-Leg5Ac7Ac donors. The various acceptors tested were LacNAc or Galβ-1,4-GlcNAc-β-FCHASE, Lacto-N-biose or Galβ-1,3-GlcNAc-β-FCHASE, TAg or Galβ-1,3-GalNAc-α-FCHASE, and Pk or Galα-1,4-Galβ-1,4-Glc-β-FCHASE. Lst enzyme preparations (2.5 μg per assay) were incubated with 2.5 pmoles of each acceptor with either 3 mM CMP-Neu5Ac or 3 mM CMP-Leg5Ac7Ac for either 2 or 20 h as indicated. Reactions were then examined by TLC. Arrows indicate the general vicinity of FCHASE acceptors (top spots), whereas arrowheads indicate the general vicinity of modified FCHASE acceptors (bottom spots—enzyme product) (FIG. 11).

Materials and Methods

Synthesis of CMP-Nonulosonate (CMP-NulO) Compounds

Neu5Ac, Neu5Gc and Neu5Ac9Az nonulosonates were purchased from commercial sources (Inalco Pharmaceuticals, Sigma, Sussex Research Laboratories Inc.). Neu5Ac9Ac and Neu5Gc8Me were synthesized using published methods (32, 33). Leg5Ac7Ac and Pse5Ac7Ac were enzymatically prepared using the methods in ref. 34 and ref. 35, respectively. In general, CMP-activation of nonulosonate sugars was performed enzymatically using appropriate CMP-sialic acid, CMP-legionaminic acid and CMP-pseudaminic acid synthetases from either *N. meningitidis, C. jejuni* or *Helicobacter pylori* (34-38). Typically, reactions contained 50 mM Tris pH 8-9, 50 mM $MgCl_2$, 15.7 mM CTP, 15 mM nonulosonate, 4 units pyrophosphatase per mmole of CTP, and sufficient quantities of CMP-NulO synthetase enzyme to obtain optimal conversion at 5-6 hours. The CMP-NulO enzymatic reactions were then passed through an Amicon Ultra-15 (10,000 molecular weight cut-off) or Ultra-4 (5,000 molecular weight cut-off) filter membrane before purification. The filtered CMP-NulO samples were then lyophilized and desalted/purified using a Superdex Peptide 10/300 GL (GE Healthcare) column in ammonium bicarbonate or NaCl solutions. For further purity, elution fractions containing respective CMP-NulOs from above were subjected to anion-exchange chromatography (Mono Q 4.6/100 PE, GE Healthcare) using either an ammonium bicarbonate or NaCl gradient. If using a NaCl gradient CMP-NulOs were then subjected to a further gel filtration (Superdex Peptide 10/300 GL) desalting using 1 mM NaCl. Quantification of CMP-NulO preparations was determined using the molar extinction coefficient of CMP (ε260=7,400). The pure fractions were diluted with water, and sodium hydroxide or NaCl was added to give approximately 2 molar equivalents of NaOH or NaCl for every mole of CMP-NulO preparation, prior to lyophilization.

For structural characterization of CMP-nonulosonates, purified material was dissolved in >99% $D_2O$. Structural analysis was performed using a Varian Inova 500 MHz ($^1$H) spectrometer with a Varian Z-gradient 3 mm probe, or a Varian 600 MHz ($^1$H) spectrometer with a Varian 5 mm Z-gradient probe. All spectra were referenced to an internal acetone standard ($\delta_H$ 2.225 ppm and $\delta_C$ 31.07 ppm). Results are shown in Table 2 verifying the production of each CMP-nonulosonate compound, except for compounds CMP-LegAc7Ac and CMP-Pse5Ac7Ac, which were confirmed based on NMR data presented in ref. 34 and ref. 35.

CMP-NulO compounds prepared were also characterized using CE-MS analysis. For CE-MS, mass spectra were acquired using an API3000 mass spectrometer (Applied Biosystems/Sciex, Concord, ON, Canada). CE was performed using a Prince CE system (Prince Technologies, Netherlands). CE separation was obtained on a 90 cm length of bare fused-silica capillary (365 um OD×50 um ID) with CE-MS coupling using a liquid sheath-flow interface and isopropanol:methanol (2:1) as the sheath liquid. An aqueous buffer comprising 30 mM morpholine (adjusted to pH9 with formic acid) was used for all experiments in the negative-ion mode. Results verifying the production of each CMP-nonulosonate compound are shown in Table 3, where observed m/z ions from CE-MS correspond accurately to the calculated masses.

Bacterial Strains and Growth Conditions

A mutant of *N. gonorrhoeae* strain F62 (8) that lacked expression of lipooligosaccharide glycosyltransferase D (lgtD), called F62 ΔlgtD (9), was provided by Dr. Daniel C. Stein (University of Maryland). LgtD adds a GalNAc residue to the terminal Gal of the Hepl lacto-N-neotetraose species (10). Therefore, any extension of the Hepl of *N. gonorrhoeae* F62 ΔlgtD is limited to the addition of a nonulosonic acid residue that is transferred from the CMP-nonulosonate added to growth media.

Bacteria (F62 ΔlgtD) grown overnight on chocolate agar plates were suspended in gonococcal liquid media supplemented with IsoVitaleX (11) that contained specified concentrations of the CMP-nonulosonate. Bacteria were then incubated at 37° C. for the period specified in each experiment.

Antibodies

Anti-fH mAb (Quidel, catalog no. A254 (mAb 90×)) or goat anti-human fH were used in flow cytometry assays to detect human fH binding to bacteria. Goat polyclonal antibodies against C3, C4 and factor B were from Complement Technology, Inc (Tyler, Tex.). Alkaline phosphatase conjugated anti-human IgG and IgM were from Sigma (St. Louis, Mo.). mAb 3F11 (mouse IgM; provided by Dr. Michael A. Apicella, University of Iowa) binds to the unsialylated Hepl lacto-N-neotetraose structure; sialylation of LOS results in decreased binding of mAb 3F11 (12). MAb 2-8C-4-1 (13) recognizes Neisserial H.8 lipoprotein and was used in whole cell ELISA assays to measure capture of bacteria on microtiter wells. FITC conjugated anti-mouse IgG and anti-goat IgG, and alkaline phosphatase conjugated anti-mouse IgM, anti-mouse IgG and anti-goat IgG were all from Sigma.

SDS-PAGE and Western Blotting for LOS Analysis

Gonococcal lysates treated with protease K (100 μg/ml) and NuPAGE® LDS Sample Buffer (4×) (Invitrogen) were separated on NuPAGE® 12% Bis-Tris (Invitrogen) gels using Novex® MES running buffer (Invitrogen) followed by sliver staining with the Bio-Rad Silver Stain Kit, or were transferred to an Immobilon PVDF membrane (Millipore). Membranes were blocked with PBS/1% milk and probed with tissue culture supernatants that contained mAb 3F11. mAb 3F11-reactive LOS bands were disclosed with anti-mouse IgM conjugated to alkaline phosphatase followed by the addition of BCIP®/NBT-Purple Liquid Substrate (Sigma).

Flow Cytometry for Factor H Binding fH binding to bacteria was performed using flow cytometry as described previously (14). Briefly, bacteria (F62 ΔlgtD) were harvested from chocolate agar plates and grown in liquid media that contained the specified concentration of the CMP-nonulosonate as described above. Bacteria were then washed with Hanks Balanced Salt Solution (HBSS) containing 1 mM $Ca^{2+}$ and 1 mM $Mg^{2+}$ ($HBSS^{++}$) and incubated with fH purified from human plasma (Complement Technology, Inc.; concentration specified for each experiment). Bound fH was detected using either anti-fH mAb (Quidel, catalog no. A254 (mAb 90×)) or goat anti-human fH, followed by FITC conjugated anti-mouse IgG or anti-goat IgG, respectively (Sigma); both Abs had similar performance characteristics. All reaction mixtures were carried out in $HBSS^{++}$/1% BSA in a final volume of 50 μl. Flow cytometry was performed using a FACSCalibur instrument (Becton Dickinson) and data were analyzed using FlowJo (version 7.2.5; Tree Star, Inc.).

Whole Cell ELISA for Complement Component Deposition

C3 and C4 fragment deposition on, and factor B binding to bacteria were measured by whole cell ELISA as described previously (14, 15). Briefly, $2\times10^8$ organisms in $HBSS^{++}$ were incubated with NHS (at concentrations of 3.3% or 10%) in a reaction volume of 100 μl for 10 min at 37° C. This time point was chosen based on the kinetics of complement deposition on gonococci in previously published data (15). Reactions were stopped after 10 min by washing three times with ice-cold HBSS containing 5 mM phenylmethylsulfonyl fluoride at 4° C. Organisms were resuspended in 200 μl of the same buffer, and 50 μl of each sample applied per well of a 96-well U-bottomed polystyrene microtiter plate (Dynatech Laboratories, Inc., Chantilly, Va.) and incubated for 3 h at 37° C. Plates were washed with PBS containing 0.05% Tween 20. Primary antibodies (polyclonal goat anti-human C3, C4 and factor B) were diluted in PBS, and secondary antibodies diluted in PBS-0.05% Tween 20 prior to use. To ensure similar capture of bacteria incubated under different conditions, the amount of gonococcal H.8 antigen (16) expression using MAb 2-8C-4-1 (13), followed by anti-mouse IgG-alkaline phosphatase conjugate, was measured.

Serum Bactericidal Assay

Serum bactericidal assays were performed as described previously (11). Bacteria harvested from an overnight culture on chocolate agar plates were grown in liquid media containing the specified concentration of CMP-nonulosonate as specified for each experiment. Approximately 2000 CFU of F62 ΔlgtD were incubated with NHS (concentration specified for each experiment). The final reaction volumes were maintained at 150 μl. Aliquots of 25 μl of reaction mixtures were plated onto chocolate agar in duplicate at the beginning of the assay ($t_0$) and again after incubation at 37° C. for 30 min ($t_{30}$). Survival was calculated as the number of viable colonies at $t_{30}$ relative to $t_0$.

Assessment of *N. gonorrhoeae* Lst Sialyltransferase Acceptor Specificity with CMP-Neu5Ac and CMP-Leg5Ac7Ac Donors Lst sialyltransferase from *N. gonorrhoeae* F62 was recombinantly produced in *Escherichia coli*. Total membranes were isolated by ultracentrifugation at 100,000×g, resuspended in 0.2% Triton X-100, 50 mM Tris pH 7.5, 100 mM NaCl and incubated for 2 h at 4° C. Solubilized membrane supernatants were then collected after another ultracentrifugation step, where Lst was found to be near purity. *N. gonorrhoeae* Lst enzymatic assays were performed using 2.5 pmoles of 4 different FCHASE acceptors; LacNAc or Galβ-1,4-GlcNAc-β-FCHASE, Lacto-N-biose or Galβ-1,3-GlcNAc-β-FCHASE, TAg or Galβ-1,3-GalNAc-α-FCHASE, Pk or Galα-1,4-Galβ-1,4-Glc-β-FCHASE. CMP-Neu5Ac donor assays contained 50 mM Tris pH 7.5, whereas CMP-Leg5Ac7Ac donor assays contained 50 mM MES pH 6. All reactions contained 10 mM $MnCl_2$, 3 mM CMP-sugar donor and 2.5 μg Lst enzyme. Reactions were incubated at 30° C. for either 2 h or 20 h as indicated. Upon completion of the reactions, stop solution was added (final concentration of 0.5% SDS, 5 mM EDTA, 25% acetonitrile) and an aliquot was run on TLC using EtOAc:MeOH:$H_2O$:HOAc 4:2:1:0.1 as the mobile phase.

The scope of the claims should not be limited by the preferred embodiments set forth in the examples, but should be given the broadest possible interpretations consistent with the description as a whole.

REFERENCES

1. Chen, X., and Varki, A. (2010) *ACS Chem Biol* 5(2), 163-176
2. Varki, A., and Gagneux, P. (2012) *Ann N Y Acad Sci* 1253, 16-36
3. Fearon, D. T. (1978) *Proc Natl Acad Sci USA* 75(4), 1971-1975
4. Kajander, T., Lehtinen, M. J., Hyvarinen, S., Bhattacharjee, A., Leung, E., Isenman, D. E., Meri, S., Goldman, A., and Jokiranta, T. S. (2011) *Proc Natl Acad Sci USA* 108(7), 2897-2902
5. Severi, E., Hood, D. W., and Thomas, G. H. (2007) *Microbiology* 153(Pt 9), 2817-2822
6. Elkins, C., Carbonetti, N. H., Varela, V. A., Stirewalt, D., Klapper, D. G., and Sparling, P. F. (1992) *Mol Microbiol* 6(18), 2617-2628
7. Ram, S., Sharma, A. K., Simpson, S. D., Gulati, S., McQuillen, D. P., Pangburn, M. K., and Rice, P. A. (1998) *J Exp Med* 187(5), 743-752
8. Schneider, H., Griffiss, J. M., Williams, G. D., and Pier, G. B. (1982) *J Gen Microbiol* 128(Pt 1), 13-22
9. Song, W., Ma, L., Chen, R., and Stein, D. C. (2000) *J Exp Med* 191(6), 949-960
10. Yang, Q. L., and Gotschlich, E. C. (1996) *J Exp Med* 183(1), 323-327
11. McQuillen, D. P., Gulati, S., and Rice, P. A. (1994) *Methods Enzymol* 236, 137-147
12. Yamasaki, R., Nasholds, W., Schneider, H., and Apicella, M. A. (1991) *Mol Immunol* 28(11), 1233-1242
13. Ram, S., Ngampasutadol, J., Cox, A. D., Blom, A. M., Lewis, L. A., St Michael, F., Stupak, J., Gulati, S., and Rice, P. A. (2007) *Infect Immun*
14. Gulati, S., Agarwal, S., Vasudhev, S., Rice, P. A., and Ram, S. (2012) *J Immunol* 188(7), 3416-3425
15. McQuillen, D. P., Gulati, S., Ram, S., Turner, A. K., Jani, D. B., Heeren, T. C., and Rice, P. A. (1999) *J Infect Dis* 179(1), 124-135

16. Cannon, J. G. (1989) *Clin Microbiol Rev* 2 Suppl, S1-4
17. Smith, H., Cole, J. A., and Parsons, N. J. (1992) *FEMS Microbiol Lett* 79(1-3), 287-292
18. Emond, J. P., Dublanchet, A., and Goldner, M. (1995) *Antonie Van Leeuwenhoek* 67(3), 281-288
19. Ward, M. E., Watt, P. J., and Glynn, A. A. (1970) *Nature* 227(256), 382-384
20. Nairn, C. A., Cole, J. A., Patel, P. V., Parsons, N. J., Fox, J. E., and Smith, H. (1988) *J Gen Microbiol* 134(Pt 12)), 3295-3306
21. Parsons, N. J., Ashton, P. R., Constantinidou, C., Cole, J. A., and Smith, H. (1993) *Microb Pathog* 14(4), 329-335
22. Mandrell, R. E., Lesse, A. J., Sugai, J. V., Shero, M., Griffiss, J. M., Cole, J. A., Parsons, N. J., Smith, H., Morse, S. A., and Apicella, M. A. (1990) *J Exp Med* 171(5), 1649-1664
23. Gulati, S., Cox, A., Lewis, L. A., Michael, F. S., Li, J., Boden, R., Ram, S., and Rice, P. A. (2005) *Infect Immun* 73(11), 7390-7397
24. Zaleski, A., and Densen, P. (1996) Sialylation of LOS inhibits gonococcal killing primarily through an effect on classical pathway activation. In: Zollinger, W. D., Frasch, C. E., and Deal, C. D. (eds). *Abstracts of the Tenth International Pathogenic Neisseria Conference*, National Institutes of Health, Baltimore, Md.
25. Madico, G., Ram, S., Getzlaff, S., Prasad, A., Gulati, S., Ngampasutadol, J., Vogel, U., and Rice, P. A. (2004) Sialylation of lacto-N-tetraose lipooligosaccharide in gonococci, but not meningococci, results in enhanced factor H binding: the modulatory role of gonococcal porin. In. 14*th International Pathogenic Neisseria Conference*, Milwaukee, Wis.
26. Michalek, M. T., Mold, C., and Bremer, E. G. (1988) *J Immunol* 140(5), 1588-1594
27. Lewis, L. A., Ram, S., Prasad, A., Gulati, S., Getzlaff, S., Blom, A. M., Vogel, U., and Rice, P. A. (2008) *Infect Immun* 76(1), 339-350
28. Ferreira, V. P., Pangburn, M. K., and Cortes, C. (2010) *Mol Immunol* 47(13), 2187-2197
29. Chou, H. H., Takematsu, H., Diaz, S., Iber, J., Nickerson, E., Wright, K. L., Muchmore, E. A., Nelson, D. L., Warren, S. T., and Varki, A. (1998) *Proc Natl Acad Sci USA* 95(20), 11751-11756
30. Ngampasutadol, J., Ram, S., Gulati, S., Agarwal, S., Li, C., Visintin, A., Monks, B., Madico, G., and Rice, P. A. (2008) *J Immunol* 180(5), 3426-3435
31. Wu, H., and Jerse, A. E. (2002) Sialylation of gonococcal LOS occurs during experimental murine gonococcal genital tract infection. In: Caugant, D. A., and Wedege, E. (eds). 13*th International Pathogenic Neisseria Conference*, Oslo, Norway
32. Ogura et al., 1987, Carbohydrate Research 167: 77-86.
33. Yu et al., 2011, Bioorganic & Medicinal Chemistry Letters 21: 5037-5040.
34. Schoenhofen et al., 2009, Glycobiology 19: 715-725.
35. Schoenhofen et al., 2006, Glycobiology 16: 8C-14C.
36. Gilbert et al., 1997, Biotechnology Letters 19: 417-420.
37. Guerry et al., 2000, Infection and Immunity 68: 6656-6662.
38. Li et al., 2012, Appl. Microbiol. Biotechnol. 93: 2411-2423.
39. Watson et al., 2011, Glycobiology 21: 99-108.
40. Yu et al., 2004, Bioorganic & Medicinal Chemistry 12: 6427-6435.
41. Mas Pons et al., 2014, Angew. Chem. Int. Ed. 53: 1275-1278.
42. Yi et al., 2013, Adv. Synth. Catal 355: 3597-3612.
43. Manzi et al., 1990, J. Biol. Chem. 265: 8094-8107.
44. Mizanur and Pohl, 2008, Appl. Microbiol. Biotechnol. 80: 757-765.
45. Varki, 1992, Glycobiology 2: 25-40.
46. Du et al., 2009, Glycobiology 19: 1382-1401.
47. Song et al., 2011, J. Biol. Chem. 286: 31610-31622.
48. Varki, A., et al, editors. Essentials of Glycobiology. 2nd edition, Cold Spring Harbor (N.Y.): Cold Spring Harbor Laboratory Press; 2009. Chapter 14.
49. Gross et al., 1987, Eur. J. Biochem. 168: 595-602.
50. Tiralongo and Schauer, 2004, Trends in Glycoscience and Glycotechnology 16: 1-15.
51. Jerse A E, Wu H, Packiam M, Vonck R A, Begum A A, Garvin L E. Estradiol-Treated Female Mice as Surrogate Hosts for *Neisseria gonorrhoeae* Genital Tract Infections. Front Microbiol 2011; 2:107.
52. Ohnishi M, Golparian D, Shimuta K, Saika T, Hoshina S, Iwasaku K, Nakayama S, Kitawaki J, Unemo M. Is *Neisseria gonorrhoeae* initiating a future era of untreatable gonorrhea?: detailed characterization of the first strain with high-level resistance to ceftriaxone. Antimicrob Agents Chemother 2011; 55:3538-45.

TABLE 1

Summary of nonose incorporation onto LOS and its functional consequences

| Nonose | Incorporated onto LOS | fH binding | Serum resistance |
|---|---|---|---|
| Neu5Ac | + | high | high$^B$ |
| Neu5Gc | + | high | high |
| Neu5Ac9Ac | + | intermediate | low$^C$ |
| Neu5Ac9Az | + | minimal$^A$ | none |
| Neu5Gc8Me | + | minimal | low |
| Leg5Ac7Ac | + | minimal | none |
| Pse5Ac7Ac | − | NA | NA |

$^A$compared to unsialylated gonococci
$^B$>100% survival in 10% serum
$^C$>100% survival in 3.3% serum and <10% survival in 10% serum

TABLE 2

| | | | | |
|---|---|---|---|---|
| NMR chemical shifts δ (ppm) for CMP-5-acetamido-3,5-dideoxy-D-glycero-D-galacto-nonulosonic acid (CMP-Neu5Ac). | | | | |
| CMP-Neu5Ac | H3ax | 1.65 | | |
| | H3eq | 2.49 | C3 | 42.2 |
| | H4 | 4.07 | C4 | 68.0 |
| | H5 | 3.95 | C5 | 52.8 |
| | H6 | 4.14 | C6 | 72.9 |
| | H7 | 3.45 | C7 | 70.0 |
| | H8 | 3.94 | C8 | 70.7 |
| | H9 | 3.62; 3.89 | C9 | 64.0 |
| NMR chemical shifts δ (ppm) for CMP-5-hydroxyacetamido-3,5-dideoxy-D-glycero-D-galacto-nonulosonic acid (CMP-Neu5Gc). | | | | |
| CMP-Neu5Gc | H3ax | 1.67 | | |
| | H3eq | 2.51 | C3 | 42.4 |
| | H4 | 4.18 | C4 | 67.8 |
| | H5 | 4.04 | C5 | 52.7 |
| | H6 | 4.25 | C6 | 72.8 |
| | H7 | 3.44 | C7 | 70.0 |
| | H8 | 3.95 | C8 | 70.9 |
| | H9 | 3.63; 3.88 | C9 | 64.2 |
| NMR chemical shifts δ (ppm) for CMP-5-acetamido-9-azido-3,5,9-trideoxy-D-glycero-D-galacto-nonulosonic acid (CMP-Neu5Ac9Az). | | | | |
| CMP-Neu5Ac9Az | H3ax | 1.65 | | |
| | H3eq | 2.49 | C3 | 42.4 |

TABLE 2-continued

| | | | | |
|---|---|---|---|---|
| | H4 | 4.07 | C4 | 68.2 |
| | H5 | 3.95 | C5 | 53.1 |
| | H6 | 4.15 | C6 | 72.9 |
| | H7 | 3.48 | C7 | 70.5 |
| | H8 | 4.07 | C8 | 69.7 |
| | H9 | 3.51; 3.64 | C9 | 54.5 |
| NMR chemical shifts δ (ppm) for CMP-5-acetamido-9-O-acetyl-3,5-dideoxy-D-glycero-D-galacto-nonulosonic acid (CMP-Neu5Ac9Ac). | | | | |
| CMP-Neu5Ac9Ac | H3ax | 1.66 | | |
| | H3eq | 2.49 | C3 | 42.1 |
| | H4 | 4.08 | C4 | 67.9 |
| | H5 | 3.97 | C5 | 52.8 |
| | H6 | 4.17 | C6 | 72.7 |
| | H7 | 3.51 | C7 | 69.7 |
| | H8 | 4.15 | C8 | 68.1 |
| | H9 | 4.16; 4.39 | C9 | 67.1 |
| NMR chemical shifts δ (ppm) for CMP-5-hydroxyacetamido-8-O-methyl-3,5-dideoxy-D-glycero-D-galacto-nonulosonic acid (CMP-Neu5Gc8Me). | | | | |
| CMP-Neu5Gc8Me | H3ax | 1.74 | | |
| | H3eq | 2.62 | C3 | 41.6 |
| | H4 | 4.20 | C4 | 67.9 |
| | H5 | 4.01 | C5 | 52.9 |
| | H6 | 4.16 | C6 | 73.3 |
| | H7 | 3.60 | C7 | 68.7 |
| | H8 | 3.59 | C8 | 81.7 |
| | H9 | 3.68; 4.03 | C9 | 60.7 |

TABLE 3

| Compound | Observed m/z | Calculated mass | Formula (M) | Comments |
|---|---|---|---|---|
| CMP-Pse5Ac7Ac | 638.5 | 639.5 | C22H34O15N5P | [M − H]⁻ |
| CMP-Leg5Ac7Ac | 638.4 | 639.5 | C22H34O15N5P | [M − H]⁻ |
| CMP-Neu5Ac | 613.5 | 614.4 | C20H31N4O16P | [M − H]⁻ |
| CMP-Neu5Gc | 629.3 | 630.5 | C20H31N4O17P | [M − H]⁻ |
| CMP-Neu5Gc8Me | 643.3 | 644.5 | C21H33N4O17P | [M − H]⁻ |
| CMP-Neu5Ac9Ac | 655.5 | 656.5 | C22H33N4O17P | [M − H]⁻ |
| CMP-Neu5Ac9Az | 638.3 | 639.5 | C20H30N7O15P | [M − H]⁻ |

TABLE 4

Effect of CMP-NulOs on complement resistance of Ng 398078 (expresses $P^K$-like structure on HepI)

| CMP-NulO [A] | % survival [mean (range)] [B,C] |
|---|---|
| None (unsialylated) | 3.6 (2.4) |
| CMP-Neu5Ac | 57.5 (1.6) |
| CMP-Leg5Ac7Ac | 0 (0) |
| CMP-Neu5Ac9Az | 7.1 (2.3) |
| CMP-Neu5Ac → CMP-Leg5Ac7Ac [D] | 0 (0) |
| CMP-Neu5Ac → CMP-Neu5Ac9Az [D] | 7.5 (5.2) |

[A] All NulOs were used at 20 μg/ml
[B] survival measured in 10% normal human serum (NHS)
[C] controls with heat-inactivated NHS showed >100% survival
[D] CMP-NulO added to media 15 min after CMP-Neu5Ac

The invention claimed is:

1. A method for identifying a cytidine 5'-monophospho-nonulosonate (CMP-nonulosonate) sugar capable of reducing virulence of *N. gonorrhoeae* comprising:

incubating a control culture of *N. gonorrhoeae* with a first CMP-nonulosonate sugar under conditions that result in incorporation of the nonulosonate sugar of the first CMP-nonulosonate sugar into lipooligosaccharide of the *N. gonorrhoeae;* incubating a test culture of *N. gonorrhoeae* with the first CMP-nonulosonate sugar and a second CMP-nonulosonate sugar under conditions that result in incorporation of the nonulosonate sugar of the first CMP-nonulosonate sugar into lipooligosaccharide of the *N. gonorrhoeae*; and determining if serum resistance of the test culture of *N. gonorrhoeae* after incubation with the first and second CMP-nonulosonate sugars is Rower than serum resistance of the control culture of *N. gonorrhoeae* after incubation with the first CMP-nonulosonate sugar, wherein the first CMP-nonulosonate sugar is a CMP-nonulosonate sugar that is able to confer serum resistance to serum-sensitive *N. gonorrhoeae.*

2. The method according to claim 1 wherein the serum resistance is determined by measuring factor H binding.

3. The method according to claim 1 wherein the serum resistance is determined by measuring C4 deposition.

4. The method according to claim 1 wherein the serum resistance is determined by measuring IgG binding.

5. The method according to claim 1, wherein the first CMP-nonulosonate sugar is a CMP-sialic acid.

6. The method according to claim 1, wherein the first CMP-nonulosonate sugar is cytidine 5'-monophospho-N-glycolylneuraminic acid (CMP-Neu5Gc).

7. The method according to claim 1, wherein the first CMP-nonulosonate sugar is cytidine 5'-monophospho-N-acetylneuraminic acid (CMP-Neu5Ac).

8. The method according to claim 1, wherein incubation of the test culture with the first CMP-nonulosonate sugar is initiated prior to incubation of the test culture with the second CMP-nonulosonate sugar.

9. The method according to claim 8, wherein the first CMP-nonulosonate sugar is cytidine 5'-monophospho-N-glycolylneuraminic acid (CMP-Neu5Gc).

10. The method according to claim 8, wherein the first CMP-nonulosonate sugar is cytidine 5'-monophospho-N-acetylneuraminic acid (CMP-Neu5Ac).

11. The method according to claim 8, wherein the serum resistance is determined by at least one of measuring factor H binding, measuring C4 deposition, and measuring IgG binding.

12. The method according to claim 1, wherein the first CMP-nonulosonate sugar and the second CMP-nonulosonate sugar are added to the test culture of *N. gonorrhoeae* at the same time.

13. The method according to claim 12, wherein the first CMP-nonulosonate sugar is cytidine 5'-monophospho-N-glycolylneuraminic acid (CMP-Neu5Gc).

14. The method according to claim 12, wherein the first CMP-nonulosonate sugar is cytidine 5'-monophospho-N-acetylneuraminic acid (CMP-Neu5Ac).

15. The method according to claim 12, wherein the serum resistance is determined by at least one of measuring factor H binding, measuring C4 deposition, and measuring IgG binding.

16. A method for identifying a cytidine 5'-monophospho-nonulosonate (CMP-nonulosonate) sugar capable of reducing virulence of *N. gonorrhoeae*, the method comprising:

incubating a control culture of *N. gonorrhoeae* with cytidine 5'-monophospho-N-glycolylneuraminic acid (CMP-Neu5Gc) under conditions that result in incorporation of the nonulosonate sugar of CMP-Neu5Gc into lipooligosaccharide of the *N. gonorrhoeae;* incubating a test culture of *N. gonorrhoeae* with a second CMP-nonulosonate sugar under conditions suitable for incorporation of the nonulosonate sugar of the second CMP-nonulosonate sugar into lipooligosaccharide of the *N. gonorrhoeae*; and determining if serum resistance of the test culture of *N. gonorrhoeae* after incubation with the second CMP-nonulosonate sugar is lower than serum resistance of the control culture of *N. gonorrhoeae* after incubation with CMP-Neu5Gc, wherein the control culture of *N. gonorrhoeae* is serum sensitive prior to incubation with the CMP-Neu5Gc, and wherein the test culture of *N. gonorrhoeae* is serum sensitive prior to incubation with the second CMP-nonulosonate sugar.

17. The method according to claim 16, further comprising determining if the nonulosonate sugar from the second CMP-nonulosonate sugar has been incorporated into lipooligosaccharide of the *N. gonorrhoeae*.

18. The method according to claim 16, wherein the serum resistance is determined by at least one of measuring factor H binding, measuring C4 deposition, and measuring IgG binding.

* * * * *